US010532011B2

(12) United States Patent
Giron et al.

(10) Patent No.: US 10,532,011 B2
(45) Date of Patent: Jan. 14, 2020

(54) TRANSFER DEVICE FOR MAKING UP KERATIN MATERIALS

(71) Applicant: L'OREAL, Paris (FR)

(72) Inventors: Franck Giron, Lagny sur Marne (FR); Henri Samain, Bievres (FR); Géraldine Fack, Levallois Perret (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 15/108,292

(22) PCT Filed: Dec. 19, 2014

(86) PCT No.: PCT/IB2014/067132
§ 371 (c)(1),
(2) Date: Jun. 25, 2016

(87) PCT Pub. No.: WO2015/097614
PCT Pub. Date: Jul. 2, 2015

(65) Prior Publication Data
US 2016/0317403 A1 Nov. 3, 2016

(30) Foreign Application Priority Data
Dec. 27, 2013 (FR) ..................... 13 63627

(51) Int. Cl.
A61K 8/06 (2006.01)
A61K 8/02 (2006.01)
A61K 8/37 (2006.01)
A61Q 1/02 (2006.01)
A61K 8/898 (2006.01)
A61K 8/34 (2006.01)
A61K 8/35 (2006.01)
A61K 8/58 (2006.01)
A61K 8/92 (2006.01)
B41J 2/005 (2006.01)
C09D 11/023 (2014.01)
C09D 11/102 (2014.01)
C09D 11/32 (2014.01)
C09D 11/38 (2014.01)

(52) U.S. Cl.
CPC ............ A61K 8/068 (2013.01); A61K 8/0204 (2013.01); A61K 8/34 (2013.01); A61K 8/345 (2013.01); A61K 8/35 (2013.01); A61K 8/37 (2013.01); A61K 8/585 (2013.01); A61K 8/898 (2013.01); A61K 8/922 (2013.01); A61Q 1/025 (2013.01); B41J 2/0057 (2013.01); C09D 11/023 (2013.01); C09D 11/102 (2013.01); C09D 11/32 (2013.01); C09D 11/38 (2013.01); A61K 2800/21 (2013.01); A61K 2800/43 (2013.01); A61K 2800/59 (2013.01); A61K 2800/87 (2013.01)

(58) Field of Classification Search
CPC ..... A61K 8/068; C09D 11/023; B41J 2/0057; A61Q 1/025
See application file for complete search history.

(56) References Cited

U.S. PATENT DOCUMENTS

| 2,746,460 A | 5/1956 | Jellinek |
| 4,137,180 A | 1/1979 | Naik et al. |
| 4,804,719 A | 2/1989 | Weaver et al. |
| 4,874,554 A | 10/1989 | Lange et al. |
| 4,925,667 A | 5/1990 | Fellows et al. |
| 4,999,418 A | 3/1991 | Krutak et al. |
| 5,030,708 A | 7/1991 | Krutak et al. |
| 5,032,670 A | 7/1991 | Parham et al. |
| 5,043,376 A | 8/1991 | Sharma et al. |
| 5,047,084 A | 9/1991 | Miller et al. |
| 5,102,980 A | 4/1992 | Krutak et al. |
| 5,104,913 A | 4/1992 | Sharma et al. |
| 5,106,942 A | 4/1992 | Krutak et al. |
| 5,194,463 A | 3/1993 | Krutak et al. |
| 5,281,659 A | 1/1994 | Weaver et al. |
| 5,913,315 A | 6/1999 | Todd |
| 5,958,560 A | 9/1999 | Ewan |
| 5,997,134 A | 12/1999 | Hotomi et al. |
| 5,997,136 A * | 12/1999 | Fujisawa ............... B41J 2/01 347/101 |
| 6,013,248 A | 1/2000 | Luebbe et al. |
| 6,106,852 A | 8/2000 | Deliquescense |

(Continued)

FOREIGN PATENT DOCUMENTS

| CN | 1476319 A | 2/2004 |
| CN | 1519278 A | 8/2004 |

(Continued)

OTHER PUBLICATIONS

Pubchem, castor oil—https://pubchenn.ncbi.nlm.nih.gov/compound/castor_oil#section=Top, 1 page, 2010.*
International Search Report and Written Opinion for PCT/IB2014/067132 dated Apr. 28, 2015 (11 pages).
Dyno Pretty Pup: "Dyno Pretty Pup Beauty Diary: LA Colors 30 Eye Design Palettes—Review." Mar. 16, 2012 (4 pages).
International Search Report for PCT/IB2014/067130 dated Mar. 11, 2015 (5 pages).
International Search Report for PCT/IB2014/067132 dated Apr. 28, 2015 (4 pages).
International Search Report for PCT/IB2014/067133 dated Mar. 11, 2015 (5 pages).
International Search Report for PCT/IB2014/067134 dated Apr. 24, 2015 (4 pages).
International Search Report for PCT/IB2014/067136 dated Jul. 7, 2015 (5 pages).

(Continued)

Primary Examiner — Kyle A Purdy
(74) Attorney, Agent, or Firm — Shumaker, Loop & Kendrick, LLP

(57) ABSTRACT

The present invention relates to a process for manufacturing a device for applying a cosmetic product by transfer onto human keratin materials, comprising the step consisting in printing, using at least one digital printer, onto a surface a cosmetic ink, the ink being in the form of an oil-in-water or water-in-oil emulsion comprising an emulsifier, the ink being liquid at 20° C.

16 Claims, 2 Drawing Sheets

(56) References Cited

U.S. PATENT DOCUMENTS

| | | | |
|---|---|---|---|
| 6,168,656 B1 * | 1/2001 | Schulz | C09D 11/36 106/31.66 |
| 6,190,730 B1 | 2/2001 | Matsos et al. | |
| 6,299,967 B1 | 10/2001 | Collins et al. | |
| 6,312,124 B1 | 11/2001 | Desormeaux | |
| 6,342,094 B1 * | 1/2002 | Kabalnov | C09D 11/30 106/31.25 |
| 6,367,484 B1 | 4/2002 | Ramin et al. | |
| 6,428,164 B1 * | 8/2002 | Missell | B41M 5/52 347/105 |
| 6,543,893 B2 | 4/2003 | Desormeaux | |
| 6,622,733 B2 | 9/2003 | Saksa | |
| 6,626,183 B1 | 9/2003 | Pietrocola | |
| 7,241,503 B2 | 7/2007 | Noguchi | |
| 8,007,062 B2 | 8/2011 | Edgar et al. | |
| 8,083,422 B1 | 12/2011 | Simmons | |
| 8,545,613 B2 | 10/2013 | Blette | |
| 8,695,610 B2 | 4/2014 | Samain | |
| 9,616,668 B1 | 4/2017 | Rabe | |
| 2002/0020422 A1 | 2/2002 | Iosilevich | |
| 2002/0061321 A1 | 5/2002 | Bara | |
| 2002/0110672 A1 | 8/2002 | Muratore-Pallatino et al. | |
| 2002/0155069 A1 | 10/2002 | Pruche | |
| 2002/0164295 A1 | 11/2002 | Scavone et al. | |
| 2003/0053976 A1 * | 3/2003 | Tournilhac | A61K 8/11 424/70.12 |
| 2004/0057742 A1 | 3/2004 | Richtsmeier | |
| 2004/0078278 A1 | 4/2004 | Dauga | |
| 2004/0241423 A1 | 12/2004 | Ramin et al. | |
| 2005/0148908 A1 | 7/2005 | Skover et al. | |
| 2006/0093943 A1 | 5/2006 | Shu et al. | |
| 2006/0098076 A1 | 5/2006 | Liang | |
| 2007/0144634 A1 | 6/2007 | Hitchcock | |
| 2008/0053476 A1 | 3/2008 | LaHood et al. | |
| 2008/0152681 A1 | 6/2008 | Brown et al. | |
| 2008/0176160 A1 | 7/2008 | Deprez et al. | |
| 2009/0325221 A1 | 12/2009 | Long et al. | |
| 2010/0031834 A1 | 2/2010 | Morgavi et al. | |
| 2010/0086693 A1 * | 4/2010 | Yamada | C09D 11/0235 427/256 |
| 2011/0020023 A1 | 1/2011 | Hirai | |
| 2011/0025040 A1 | 2/2011 | Dominguez | |
| 2011/0141188 A1 | 6/2011 | Morita | |
| 2011/0159463 A1 | 6/2011 | Samain | |
| 2011/0164263 A1 | 7/2011 | Samain et al. | |
| 2011/0268873 A1 | 11/2011 | Blette | |
| 2012/0027423 A1 | 2/2012 | Kawai | |
| 2012/0027443 A1 | 2/2012 | Takahashi et al. | |
| 2012/0244316 A1 | 9/2012 | Dobler et al. | |
| 2012/0244465 A1 | 9/2012 | Kobayashi | |
| 2012/0307304 A1 | 12/2012 | Moreno | |
| 2013/0216295 A1 | 8/2013 | Wong | |
| 2014/0233967 A1 | 8/2014 | Suzuki | |
| 2015/0053759 A1 | 2/2015 | Cahill et al. | |
| 2015/0150767 A1 | 6/2015 | Klug et al. | |
| 2016/0103962 A1 | 4/2016 | Costantino et al. | |
| 2016/0316890 A1 | 11/2016 | Samain | |
| 2016/0316891 A1 | 11/2016 | Samain | |
| 2016/0316892 A1 | 11/2016 | Giron | |
| 2016/0324298 A1 | 11/2016 | Giron | |
| 2016/0324299 A1 | 11/2016 | Samain | |

FOREIGN PATENT DOCUMENTS

| | | |
|---|---|---|
| CN | 101010064 A | 8/2007 |
| CN | 101056605 A | 10/2007 |
| CN | 101686927 A | 3/2010 |
| CN | 101980694 A | 2/2011 |
| CN | 102490540 A | 6/2012 |
| EP | 705593 A1 | 4/1996 |
| EP | 0728460 A1 | 8/1996 |
| EP | 0749746 A1 | 12/1996 |
| EP | 0749747 A1 | 12/1996 |
| EP | 780114 A1 | 6/1997 |
| EP | 0923928 A1 | 6/1999 |
| EP | 0930060 A1 | 7/1999 |
| EP | 0938887 A1 | 9/1999 |
| EP | 1000607 A1 | 5/2000 |
| EP | 1048282 A1 | 11/2000 |
| EP | 1059047 A1 | 12/2000 |
| EP | 1304056 A2 | 4/2003 |
| EP | 1925278 A1 | 5/2008 |
| EP | 2090935 A1 | 8/2009 |
| FR | 2232303 A1 | 1/1975 |
| FR | 2759941 A1 | 8/1998 |
| FR | 2792192 A1 | 10/2000 |
| FR | 2858226 A1 | 2/2005 |
| FR | 2900594 A | 8/2007 |
| FR | 2905630 A1 | 3/2008 |
| FR | 2909844 A1 | 6/2008 |
| FR | 2939033 A1 | 6/2010 |
| JP | S62180000 A | 8/1987 |
| JP | S63-188616 A | 8/1988 |
| JP | H04-208997 A | 7/1992 |
| JP | H11-007203 A | 1/1999 |
| JP | H11169231 A | 6/1999 |
| JP | 2001-245945 A | 9/2001 |
| JP | 2001278739 A | 10/2001 |
| JP | 3266197 B2 | 1/2002 |
| JP | 2002-058528 A | 2/2002 |
| JP | 2002-148998 A | 5/2002 |
| JP | 2003006452 A | 1/2003 |
| JP | 2004501177 A | 1/2004 |
| JP | 2005040356 A | 2/2005 |
| JP | 2005-088434 A | 4/2005 |
| JP | 2007204487 A | 8/2007 |
| JP | 2008-127388 A | 6/2008 |
| JP | 2010-186133 A | 8/2010 |
| JP | 2012-002869 A | 1/2012 |
| JP | 2012072081 A | 4/2012 |
| JP | 2012-518457 A | 8/2012 |
| JP | 2012-520837 A | 9/2012 |
| JP | 2012249849 A | 12/2012 |
| JP | 2013-031504 A | 2/2013 |
| JP | 2013137758 A | 7/2013 |
| JP | 2013-252709 A | 12/2013 |
| WO | 1992007913 A1 | 5/1992 |
| WO | 9848659 A1 | 5/1998 |
| WO | 02/36083 A1 | 5/2002 |
| WO | 03033270 A1 | 4/2003 |
| WO | 2006/128737 A1 | 12/2006 |
| WO | 2006128737 A1 | 12/2006 |
| WO | 2007/134171 A1 | 11/2007 |
| WO | 2010/004526 A1 | 1/2010 |
| WO | 2010004526 A1 | 1/2010 |
| WO | 2010004531 A1 | 1/2010 |
| WO | 2010/095118 A | 8/2010 |
| WO | 2010/105842 A2 | 9/2010 |
| WO | 2012081065 A1 | 6/2012 |
| WO | 2013093889 A2 | 6/2013 |
| WO | 2013126513 A1 | 8/2013 |
| WO | 2013178701 A2 | 12/2013 |

OTHER PUBLICATIONS

International Search Report for PCT/IB2014/067138 dated Mar. 11, 2015 (3 pages).
Non-Final Office Action in U.S. Appl. No. 15/108,076 dated Mar. 16, 2017 (12 pages).
"Cheap laser printer paper for toner transfer?" http://www.fountainpennetwork.com/forum/topic/41250-cheap-laser-printer-paper-for-toner-transfer/,) Oct. 2, 2007 (3 pages).
"Papilio Laser Printable Temporary Tattoo Paper" (http://www.papilio.com/laser temporary tattoo paper.html), Dec. 14, 2013 (11 pages).
Non-Final Office Action in U.S. Appl. No. 15/108,192 dated Oct. 6, 2017 (6 pages).
Final Rejection for U.S. Appl. No. 15/108,076 dated Aug. 21, 2017.
Canon, fix your own printer, https://www.fixyourownprinter.com/posts/66407 (dated: Mar. 17, 2010) (1 page).
Restriction Requirement for U.S. Appl. No. 15/108,303 dated Sep. 6, 2017 (7 pages).

(56) References Cited

OTHER PUBLICATIONS

Office Action dated May 18, 2018 for Chinese Patent Application No. 2014800713416 (22 pages).
Apr. 12, 2018 Office Action issued in U.S. Appl. No. 15/108,303.
First Office Action for Chinese Patent Application No. 201480076509.2 with English Translation dated Oct. 30, 2017, 9 pages.
Office Action dated Apr. 23, 2018 in European Patent Application No. 14 833 256.2.
Office Action dated Jul. 2, 2018 issued in Japanese Patent Application No. 2016-543073 (17pp).
Office Action dated Jun. 5, 2018 issued in Chinese Patent Application No. 201480074439.7 (16 pp).
Office Action issued in Chinese Application No. 201480071272.9 dated Jul. 2, 2018 (14 pp).
Office Action issued in U.S. Appl. No. 15/108,295 dated Aug. 6, 2018 (56 pp).
Office Action issued in U.S. Appl. No. 15/108,151 dated Aug. 7, 2018 (60 pp).
Office Action dated Sep. 10, 2018 in Japanese Patent Application No. 2016-542897 (7 pages).
Office Action for JP App. No. 2016-543072 dated Dec. 17, 2018 with English Translation(7 pages).
Office Action for JP App. No. 2016-543056 dated Dec. 17, 2018 with English Translation (7 pages).
Non-Final Office Action for U.S. Appl. No. 15/108,302 dated Feb. 8, 2019 (7 pages).
Final Rejection for U.S. Appl. No. 15/108,295 dated Feb. 5, 2019 (10 pages).
Restriction Requirement for U.S. Appl. No. 15/108,305 dated Jan. 31, 2019 (8 pages).
English Translation of JP Office Action for JP Pat. App. No. 2016-542995 drafted Jan. 16, 2019 and dated Jan. 21, 2019 (3 pages).
Office Action for JP App. No. 2016-543027 dated Dec. 21, 2018 with English Translation (13 pages).
Office Action for JP App. No. 2016-543057 dated Dec. 17, 2018 with English Translation (14 pages).
Non-Final Office Action for U.S. Appl. No. 15/108,294 dated Mar. 4, 2019 (11 pgs.).
Final Rejection for U.S. Appl. No. 15/108,151 dated May 20, 2019 (11 pages).
Non-Final Office Action for U.S. Appl. No. 15/108,305 dated May 15, 2019 (17 pages).
Non-Final Office Action for U.S. Appl. No. 15/108,295 dated Jun. 6, 2019 (12 pages).
Chinese Office Action dated Dec. 5, 2018 in Chinese Application No. 201480071307.9 (8 pages).
Japanese Office Action dated Nov. 19, 2018 for Japanese Application No. 2016-542996 (32 pages).
LA Colors 30 Eye Design Palettes—Review, Dyno Pretty Pup, http://dynopupbeauty.blogspot.nl/2012/03/la-colors-30-eye-design-palettes-review.html, Mar. 16, 2012 (5 pages).
Notice of Allowance dated Nov. 13, 2018 issued in U.S. Appl. No. 15/108,303 (27 pages).
Japanese Office Action for JP Pat. Appln. No. 2016-542897, dated Sep. 17, 2019 (10 pages).
Final Rejection for U.S. Appl. No. 15/108,302 dated Jul. 2, 2019 (7 pages).
Notice of Allowance for U.S. Appl. No. 15/108,294 dated Jul. 25, 2019 (9 pages).
Japanese Office Action for JP Pat. Appln. No. 2016-543057 dated Aug. 26, 2019 (8 pages).
Japanese Office Action for JP Pat. Appln. No. 2016-543056 dated Aug. 26, 2019 (8 pages).
Japanese Office Action for JP Pat. Appln. No. 2016-542996 dated Sep. 2, 2019 (14 pages).

\* cited by examiner

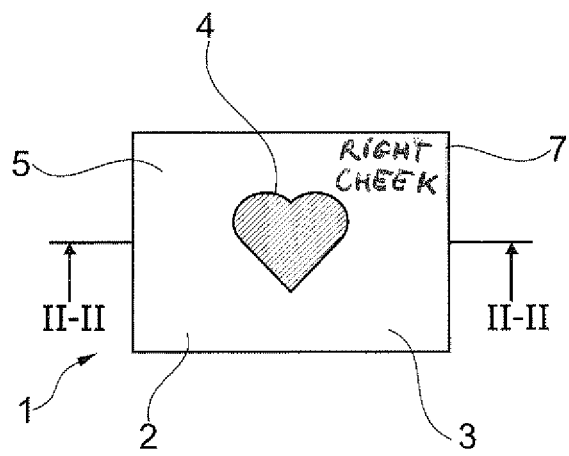
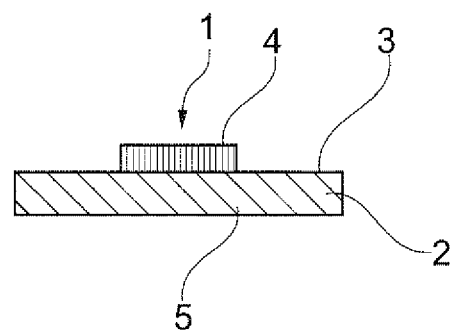
Fig. 1    Fig. 2
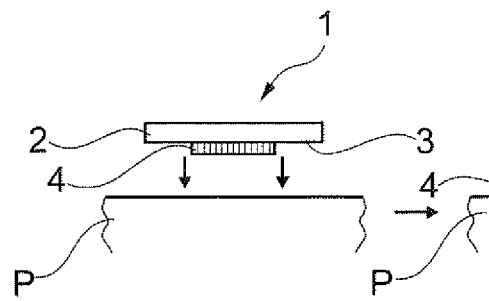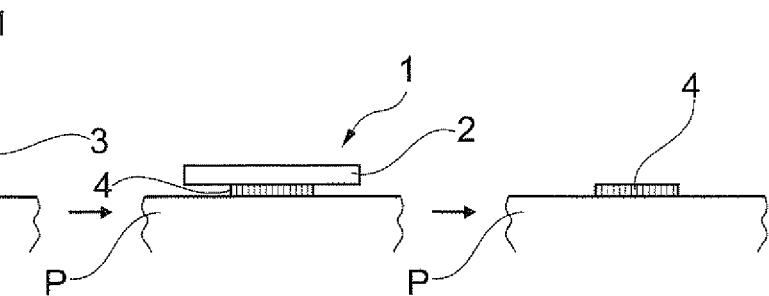
Fig. 3    Fig. 4    Fig. 5
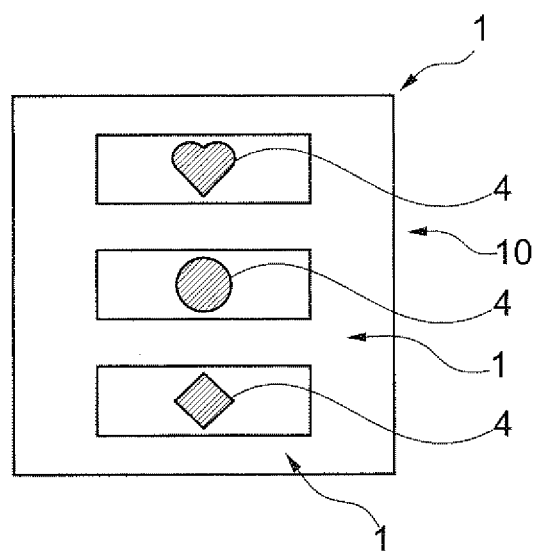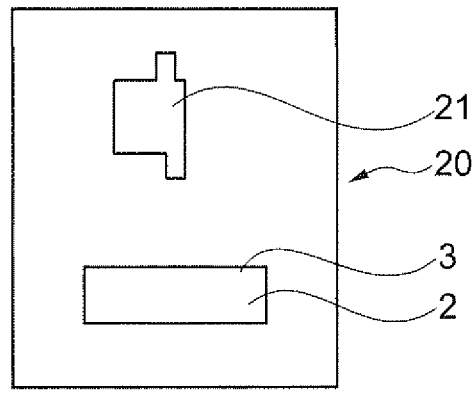
Fig. 6    Fig. 7

TRANSFER DEVICE FOR MAKING UP KERATIN MATERIALS

The present invention relates to makeup application by transfer.

BACKGROUND

It is difficult to make up keratin materials, especially the skin, by transferring a deposit of ink printed on a substrate. The reason for this is that the known inks are such that, once the printing is performed, they dry so quickly that transfer onto the keratin materials does not take place.

One way of solving this problem is to moisten the transfer surface or the area to be treated with a suitable solvent such as water. However, this method may be unacceptable due to the fact that it is not always possible to meter out precisely the amount of solvent to be applied, which may lead to "running" making the transfer onto the keratin materials irregular and/or imprecise and thus leading to an unsatisfactory makeup result.

Moreover, it is desirable for the makeup device to provide satisfactory transfer makeup in the case of a transfer performed immediately after printing, or within 30 minutes thereof, but also in the case of a transfer performed a few days or even a few months after printing.

In addition, it is also desirable for the pattern, once transferred onto keratin materials, especially the skin, to remain relatively stable. In other words, either immediately after transferring or, for example, within an hour of transferring, it is advantageous for the made-up area to be able to be touched, especially with the fingers, without deteriorating the pattern produced.

However, conventionally produced makeup coatings may not have satisfactory stability.

This lack of stability is not necessarily a problem, if high precision of the makeup pattern is not sought. On the other hand, in the case of precise patterns obtained by printing, it is important for the makeup obtained after transferring to be stable.

There is consequently a need for makeup devices that allow transfer makeup to be obtained by simple contact, without addition of solvent, whether the user seeks to transfer the pattern just after printing or after a longer or shorter period of storage of the device.

It is also sought to have available transfer makeup devices that make it possible to obtain a stable pattern within an hour of transferring.

Oil-in-water (O/W) and water-in-oil (W/O) emulsions are well known in the field of cosmetics.

Documents EP-A-728 460 and EP-A-780 114 describe nanoemulsions based on liquid nonionic amphiphilic lipids or silicone surfactants. Nanoemulsions are also described in documents FR-A-2 787 026, FR-A-2 787 027, FR-A-2 787 325, FR-A-2 787 326, FR-A-2 787 703 and FR-A-2 787 728.

U.S. Pat. No. 5,047,084 relates to a thermal inkjet printer ink in microemulsion form comprising an aqueous phase and a water-immiscible phase, the latter being solid at room temperature and liquid at 70° C.

The present invention is directed toward meeting all or some of the needs recalled above.

SUMMARY

According to a first aspect, a subject of the present invention is a process for manufacturing a device for applying a cosmetic product by transfer onto human keratin materials, comprising the step consisting in printing, using at least one digital printer, onto a transfer surface a coat of at least one cosmetic ink, the ink being in the form of an oil-in-water (O/W) or water-in-oil (W/O) emulsion and comprising an emulsifying surfactant, the ink being liquid at 20° C.

The ink may be a makeup and/or care product.

The transfer surface is, for example, an outer surface of a substrate, especially in sheet form.

By means of the invention, the user can decorate and/or treat the skin or the hair uniformly or with patterns.

The use of a coat of cosmetic ink obtained by printing using a printer advantageously makes it possible, when compared with standard makeup applications, to obtain a complex and customizable application.

The use of an emulsion that is liquid at room temperature (20° C.) increases the range of colours that may be produced, offering a broader range of usable colours than the simple list of water-soluble dyes.

At the same time that the dyestuff is deposited, it is thus possible to deposit at least one water-immiscible compound, which, being especially fatty, firstly facilitates the transfer of the dyestuff, in particular for use on the skin, and secondly protects the dyestuff after printing and helps to conserve the device according to the invention, and finally improves the adhesion of the ink to the transfer surface, which avoids risks of detachment during the manufacture or during the handling of the device before transfer onto the keratin materials.

The emulsion increases the sharpness of the pattern transferred by making it possible to transfer the colour onto the skin without adding an intermediary composition.

In addition, it is possible to produce a cosmetic ink comprising hydrophobic dyes and water, without increasing the viscosity, which thus avoids clogging of the printer nozzles.

In one embodiment example, the cosmetic ink is printed in a predefined pattern, the process especially comprising a step of choosing and/or making the pattern by a user and of transmitting, by means of a machine connected to at least one printer that performs the printing, information related to this pattern.

The machine may be a computer, an advanced portable telephone, also known as a "smartphone", or a tablet computer. The machine may be connected physically and/or by means of a data exchange network to the said printer.

The printer is preferably an inkjet printer, for example a thermal or piezoelectric printer.

In one embodiment example, the printing is performed directly onto a non-flat transfer surface, corresponding especially to the outer surface of a roller.

Cosmetically Acceptable Medium

The cosmetic ink according to the invention constitutes a cosmetically acceptable medium, i.e. a medium that is compatible with keratin materials such as the skin of the face, the scalp or the body, the lips, the hair, the eyelashes, the eyebrows and the nails.

The cosmetic ink may comprise a dyestuff and at least one emulsion, different from the dyestuff.

The emulsion may have a viscosity at 25° C. ranging from approximately 1 mPa·s to 500 mPa·s and preferably from 1 mPa·s to 300 mPa·s.

The viscosity of an emulsion of the invention may be measured via any process known to those skilled in the art, and especially according to the following conventional process. At 25° C. using a Rheomat 180 viscometer, equipped with a spindle rotating at 200 rpm, a person skilled in the art can select the spindle for measuring the viscosity from the spindles M1, M2, M3 and M4 on the basis of their general knowledge, so as to be able to perform the measurement.

The ink advantageously comprises both a hydrophilic phase comprising one or more compounds that are miscible with water at 20° C. and an oily phase comprising one or more water-immiscible compounds.

At an ambient temperature of 20° C., the hydrophilic phase may form a dispersed phase in a continuous phase formed by the oily phase; a water-in-oil (W/O) emulsion is thus obtained.

In a preferred variant, the oily phase forms at 20° C. a dispersed phase in a continuous phase formed by the hydrophilic phase.

The emulsion may comprise oil globules with a mean size preferably between 10 nm and 100 μm and preferably between 20 nm and 50 μm.

Dyestuff

The dyestuff may comprise one or more dyes as described below. The hydrophilic phase and/or the oily phase may each comprise one or more dyes.

The invention makes it possible in particular to use dyes that do not penetrate the skin, facilitating the makeup removal.

The dyestuff may be present in the ink in a mass content ranging from 0.01% to 60%, preferably ranging from 0.1% to 40%, or even from 0.1% to 30% and preferentially ranging from 0.5% to 20%, relative to the total mass of the ink.

The colouring ink may comprise one or more dyestuffs chosen from water-soluble dyes, liposoluble dyes, pulverulent dyestuffs such as pigments, especially nacres, and glitter flakes, or alternatively colouring polymers.

The term "pigments" should be understood as meaning white or coloured, mineral or organic particles of any form, which are insoluble in the cosmetic medium, and which are intended to colour the cosmetic ink.

The term "nacres" should be understood as meaning iridescent particles of any shape, in particular produced by certain molluses in their shell, or else synthesized.

The pigments may be white, black or coloured, and mineral and/or organic. Among the mineral pigments that may be mentioned are titanium dioxide, optionally surface-treated, zirconium oxide or cerium oxide, and also zinc oxide, iron (black, yellow or red) oxide or chromium oxide, manganese violet, ultramarine blue, chromium hydrate and ferric blue, and metal powders, for instance aluminium powder and copper powder.

Among the organic pigments that may be mentioned are carbon black, pigments of D&C type and lakes based on cochineal carmine or on barium, strontium, calcium or aluminium.

The nacreous pigments may be chosen from white nacreous pigments such as mica coated with titanium or with bismuth oxychloride, coloured nacreous pigments such as titanium mica coated with iron oxides, titanium mica coated especially with ferric blue or with chromium oxide, titanium mica coated with an organic pigment and also nacreous pigments based on bismuth oxychloride.

Among the water-soluble dyes, mention may be made of the disodium salt of ponceau, the disodium salt of alizarin green, quinoline yellow, the trisodium salt of amaranth, the disodium salt of tartrazine, the monosodium salt of rhodamine, the disodium salt of fuchsin, xanthophyll and methylene blue.

Among the liposoluble dyes, mention may be made of Sudan Red II (CTFA: D&C Red 17), lutein, quinizarine green (CTFA: D&C Green 6), alizurol purple SS (CTFA: D&C Violet 2), Sudan brown, D&C yellow 11, D&C Orange 5, quinoline yellow, curcumin, carotenoid derivatives such as lycopene, beta-carotene, bixin or capsanthin, and mixtures thereof. The dyeing polymers are generally copolymers based on at least two different monomers, at least one of which is a monomeric organic dye. Such polymeric dyes are known to those skilled in the art. Reference may be made, for example, to the following documents: U.S. Pat. Nos. 5,032,670; 4,999,418; 5,106,942; 5,030,708; 5,102, 980; 5,043,376; 5,104,913; 5,281,659; 5,194,463; 4,804, 719; WO 92/07913 or EP 1 048 282.

The printing may use several different inks, especially inks of different colours.

The printing may use at least three, especially at least four, five, six, seven, eight, nine, ten, eleven or twelve cosmetic inks of different colours.

The printing may use only colouring inks that produce primary colours. As a variant, the printing may use both colouring inks that produce primary colours and at least one ink that produces a non-primary colour.

In one variant, the printing may use colouring inks that produce black and/or white. For example, a black cosmetic ink may comprise a black dyestuff chosen from carbon black and melanin. A white cosmetic ink may comprise titanium dioxide as white dyestuff.

The printing of the ink may be three-colour or four-colour printing.

The pattern obtained by printing may comprise several areas of different colours. As a variant, the pattern obtained by printing is a flat tint.

The ink may be deposited in several printing passes. In other words, a first fraction of the ink may first be printed onto the transfer surface, followed by a second fraction of the ink on all or part of the first fraction.

In one embodiment example, the substrate is coated with a coloured coating in dry form, the coating comprising a pigment and/or a dye, the coat of ink being printed onto the coating.

Emulsifier

Examples of synonyms for the term "emulsifier" are: amphiphilic lipid, surfactant, surface agent.

The term "amphiphilic lipid" means herein any molecule having a bipolar structure, i.e. comprising at least one hydrophobic part and at least one hydrophilic part and having the property of reducing the surface tension of water ($\gamma$<55 mN/m) and of reducing the interface tension between water and an oily phase.

The emulsifier may be present in the cosmetic ink according to the invention in a mass proportion ranging from 0.1% to 30% by weight and in particular from 0.5% to 20% by weight relative to the total weight of the ink.

According to a first embodiment of the invention, the ink may comprise an emulsifier for obtaining an oil-in-water emulsion.

Examples of oil-in-water emulsifiers that may be mentioned include:

oxyalkylenated (more particularly polyoxyethylenated) fatty acid esters of glycerol; oxyalkylenated (more particularly polyoxyethylenated) fatty acid esters of sorbitan; oxyalkylenated (oxyethylenated and/or oxypropylenated) fatty acid esters; oxyalkylenated (oxyethylenated and/or oxypropylenated) fatty alcohol ethers; fatty acid esters of sugars such as sucrose stearate; and mixtures thereof, such as the mixture of glyceryl stearate and PEG-40 stearate;

fatty acid esters of polyethylene glycol;

$C_{16}$-$C_{22}$ fatty acid esters of glycerol;

$C_{16}$-$C_{22}$ fatty acids;

oxyethylenated and/or oxypropylenated ethers (which may comprise from 1 to 150 oxyethylene and/or oxypropylene groups) of glycerol.

The fatty chain of the esters or ethers described previously may be a $C_{12}$-$C_{22}$ chain; it may be chosen especially from stearyl, behenyl, arachidyl, palmityl and cetyl units and mixtures thereof such as cetearyl. Preferably, the fatty chain is a stearyl chain.

The number of ethylene oxide units may range from 8 to 150, preferably from 10 to 100, better still from 10 to 60. According to one particular embodiment of the invention, this number may range from 20 to 40.

As examples of fatty acid esters of polyethylene glycol, mention may be made of stearic acid esters respectively comprising 20, 30, 40, 50 and 100 ethylene oxide units, such as the products respectively sold under the names Myrj 49 P (polyethylene glycol 20 EO stearate; CTFA name: PEG-20 stearate), Myrj 51, Myrj 52 P (polyethylene glycol 40 EO stearate; CTFA name: PEG-40 stearate), Myrj 53 and Myrj 59 P by Croda.

The fatty acid ester of glycerol may be obtained especially from an acid comprising a saturated linear alkyl chain containing from 16 to 22 carbon atoms. Fatty acid esters of glycerol that may especially be mentioned include glyceryl stearate (glyceryl mono-, di- and/or tristearate) (CTFA name: Glyceryl stearate) or glyceryl ricinoleate, and mixtures thereof. Preferably, the fatty acid ester of glycerol used is chosen from glyceryl stearates.

Use may also be made, as emulsifier, of silicone surfactants such as dimethicone copolyols (for example the product sold under the name Q2-5220® by the company Dow Corning) or dimethicone copolyol benzoate (Finsolv SLB 101 and 201® from the company Finetex).

Use may also be made, as emulsifier, of copolymers of propylene oxide and of ethylene oxide, also known as EO/PO polycondensates, and mixtures thereof.

EO/PO polycondensates are more particularly copolymers formed from polyethylene glycol and polypropylene glycol blocks, for instance polyethylene glycol/polypropylene glycol/polyethylene glycol triblock polycondensates. These triblock polycondensates have, for example, the following chemical structure:

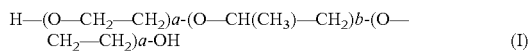

$$H—(O—CH_2—CH_2)a-(O—CH(CH_3)—CH_2)b-(O—CH_2—CH_2)a-OH \quad (I)$$

in which formula a ranges from 2 to 120 and b ranges from 1 to 100.

The EO/PO polycondensate preferably has a weight-average molecular weight ranging from 1000 to 15 000 and better still ranging from 2000 to 13 000. Advantageously, said EO/PO polycondensate has a cloud point, at 10 g/l in distilled water, of greater than or equal to 20° C., preferably of greater than or equal to 60° C. The cloud point is measured according to the standard ISO 1065.

As EO/PO polycondensate that may be used according to the invention, mention may be made of the polyethylene glycol/polypropylene glycol/polyethylene glycol triblock polycondensates sold under the name Synperonic®, such as Synperonic PE/L44® and Synperonic PE/F127®, by the company ICI.

Use may also be made of anionic surfactants, for instance the salts (in particular alkali salts, and especially of sodium, ammonium salts, amine salts, amino alcohol salts or magnesium salts) of the following compounds: alkyl sulfates, alkyl ether sulfates, alkylamido ether sulfates, alkylarylpolyether sulfates, monoglyceride sulfates; alkyl sulfonates, alkyl phosphates, alkylamide sulfonates, alkylaryl sulfonates, α-olefin sulfonates, paraffin sulfonates; ($C_6$-$C_{24}$) alkyl sulfosuccinates, ($C_6$-$C_{24}$)alkyl ether sulfosuccinates, ($C_6$-$C_{24}$)alkylamide sulfosuccinates; ($C_6$-$C_{24}$)alkyl sulfoacetates; ($C_6$-$C_{24}$)acyl sarcosinates and ($C_6$-$C_{24}$)acyl glutamates.

Use may also be made of ($C_6$-$C_{24}$)alkyl polyglycoside carboxylic esters such as alkyl glucoside citrates, alkylpolyglycoside tartrates and alkylpolyglycoside sulfosuccinates, alkylsulfosuccinamates; acyl isethionates and N-acyltaurates, the alkyl or acyl radical of all these various compounds preferably comprising from 12 to 20 carbon atoms, and the aryl radical preferably denoting a phenyl or benzyl group.

Among the anionic surfactants that may also be used, mention may also be made of fatty acid salts such as the salts of oleic, ricinoleic, palmitic and stearic acids, coconut oil acid or hydrogenated coconut oil acid; acyl lactylates in which the acyl radical contains 8 to 20 carbon atoms.

Use may also be made of alkyl-D-galactoside uronic acids and salts thereof, polyoxyalkylenated ($C_6$-$C_{24}$)alkyl ether carboxylic acids, polyoxyalkylenated ($C_6$-$C_{24}$)alkylaryl ether carboxylic acids, polyoxyalkylenated ($C_6$-$C_{24}$)alkylamido ether carboxylic acids and salts thereof, in particular those containing from 2 to 50 alkylene oxide and in particular ethylene oxide groups, and mixtures thereof.

According to the invention, among the anionic surfactants, it is preferred to use alkyl sulfates, alkyl ether sulfates and α-olefin sulfonates.

Amphoteric and/or zwitterionic surfactants may also be used. They may especially be aliphatic secondary or tertiary amine derivatives in which the aliphatic radical is a linear or branched chain comprising 8 to 22 carbon atoms and containing at least one water-soluble anionic group (for example carboxylate, sulfonate, sulfate, phosphate or phosphonate); mention may also be made of ($C_8$-$C_{20}$)alkyl betaines, sulfo betaines, ($C_8$-$C_{20}$)alkylamido($C_1$-$C_6$)alkyl betaines or ($C_8$-$C_{20}$)alkylamido($C_1$-$C_6$)alkyl sulfo betaines.

Among the amine derivatives, mention may be made of the products as described in patents U.S. Pat. Nos. 2,528,378 and 2,781,354 and having the structures:

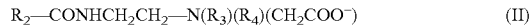

$$R_2—CONHCH_2CH_2—N(R_3)(R_4)(CH_2COO^-) \quad (II)$$

in which: $R_2$ CO denotes a $C_6$-$C_{24}$ acyl radical, for example a radical present in hydrolyzed coconut oil, an octoyl, decoyl or dodecanoyl radical, and mixtures thereof, $R_3$ denotes a beta-hydroxyethyl group and $R_4$ a carboxymethyl group; and

$$R'_2—CONHCH_2CH_2—N(B)(C) \quad (III)$$

in which:

B represents —$CH_2CH_2OX'$, C represents —$(CH_2)_z$—Y', with z=1 or 2,

X' denotes the —$CH_2CH_2$—COOH group or a hydrogen atom,

Y' denotes —COOH or the —$CH_2$—CHOH—$SO_3H$ radical, $R'_2CO$ denotes a $C_6$-$C_{24}$ acyl radical, for example a radical present in hydrolyzed coconut oil or linseed oil, or an octoyl, decoyl or dodecanoyl, stearoyl, isostearoyl or oleoyl radical, and mixtures thereof.

These compounds are classified in the CTFA dictionary, 5th edition, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium capryloamphodipropionate, lauroamphodipropionic acid and cocoamphodipropionic acid.

An example that may be mentioned is disodium cocoamphodiacetate, sold under the trade name Miranol®C2M Concentrate by the company Rhodia Chimie.

According to a second embodiment, the ink may comprise a water-in-oil emulsifier chosen from silicone emulsifiers of the alkyldimethicone copolyol type and of the dimethicone copolyol type, non-silicone W/O emulsifiers with an HLB from 3 to 7, and mixtures thereof.

Emulsifiers of the alkyldimethicone copolyol type and of the dimethicone copolyol type.

The alkyldimethicone copolyols in accordance with the invention correspond to formula (IV) below:

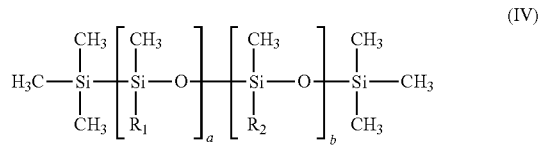

(IV)

in which:

$R_1$ denotes a linear or branched $C_{12}$-$C_{20}$ and preferably $C_{12}$-$C_{18}$ alkyl group;

$R_2$ denotes the group: —CnH2n-(—OC2H4-)x-(—OC3H6-)y-O—R3, $R_3$ denotes a hydrogen atom or a linear or branched alkyl radical comprising from 1 to 12 carbon atoms;

a is an integer ranging from 1 to about 500;

b denotes an integer ranging from 1 to about 500;

n is an integer ranging from 2 to 12 and preferably from 2 to 5;

x denotes an integer ranging from 1 to about 50 and preferably from 1 to 30;

y denotes an integer ranging from 0 to 49 approximately and preferably from 0 to 29, with the proviso that when y is other than zero, the ratio x/y is greater than 1 and preferably ranges from 2 to 11.

Among the alkyldimethicone copolyol emulsifiers of formula (IV) that are preferred, mention will be made more particularly of Cetyl PEG/PPG-10/1 Dimethicone and more particularly the mixture Cetyl PEG/PPG-10/1 Dimethicone and Dimethicone (INCI name), for instance the product sold under the trade name Abil EM90 by the company Goldschmidt, or alternatively the mixture (Polyglyceryl-4 Stearate and Cetyl PEG/PPG-10 (and) Dimethicone (and) Hexyl Laurate), for instance the product sold under the trade name Abil WE09 by the same company.

The dimethicone copolyols in accordance with the invention correspond to formula (V) below:

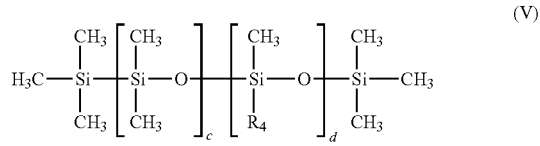

(V)

in which $R_4$ denotes the group: —CmH2m-(—OC2H4-)s-(—OC3H6-)t-O—R5, $R_5$ denotes a hydrogen atom or a linear or branched alkyl radical comprising from 1 to 12 carbon atoms;

c is an integer ranging from 1 to about 500;

d denotes an integer ranging from 1 to about 500;

m is an integer ranging from 2 to 12 and preferably from 2 to 5;

s denotes an integer ranging from 1 to about 50 and preferably from 1 to 30;

t denotes an integer ranging from 0 to about 50 and preferably from 0 to 30; with the proviso that the sum s+t is greater than or equal to 1.

Among these preferential dimethicone copolyol emulsifiers of formula (V), use will particularly be made of PEG-18/PPG-18 Dimethicone and more particularly the mixture Cyclopentasiloxane (and) PEG-18/PPG-18 Dimethicone (INCI name), such as the product sold by the company Dow Corning under the trade name Silicone DC5225 C or KF-6040 from the company Shin-Etsu.

According to a particularly preferred form, use will be made of a mixture of at least one emulsifier of formula (IV) and of at least one emulsifier of formula (V).

Use will be made more particularly of a mixture of PEG-18/PPG-18 Dimethicone and Cetyl PEG/PPG-10/1 Dimethicone and even more particularly of a mixture of (Cyclopentasiloxane (and) PEG-18/PPG-18 Dimethicone) and of Cetyl PEG/PPG-10/1 Dimethicone and Dimethicone or of (Polyglyceryl-4 Stearate and Cetyl PEG/PPG-10 (and) Dimethicone (and) Hexyl Laurate).

The total amount of emulsifiers of formula (IV) and/or of emulsifiers of formula (V) in the composition varies preferably in active material contents ranging from 0.3% to 8% by weight and more particularly from 0.5% to 4% by weight relative to the total weight of the composition.

Non-silicone W/O Emulsifiers with an HLB from 3 to 7

The water-in-oil nonionic non-silicone emulsifier may be chosen, for example, from nonionic emulsifiers derived from fatty acids and polyols, alkylpolyglycosides (APGs) and sugar esters, and mixtures thereof.

As nonionic emulsifiers derived from fatty acids and polyols, use may be made especially of fatty acid esters of polyols, the fatty acid especially containing a $C_8$-$C_{24}$ alkyl chain, and the polyols being, for example, glycerol and sorbitan.

Fatty acid esters of polyol that may especially be mentioned include isostearic acid esters of polyols, stearic acid esters of polyols, and mixtures thereof, in particular isostearic acid esters of glycerol and/or sorbitan.

Stearic acid esters of polyols that may especially be mentioned include the polyethylene glycol esters, for instance PEG-30 Dipolyhydroxystearate, such as the product sold under the name Arlacel P135 by the company ICI.

Examples of glycerol and/or sorbitan esters that may be mentioned include polyglyceryl isostearate, such as the product sold under the name Isolan GI 34 by the company Goldschmidt; sorbitan isostearate, such as the product sold under the name Arlacel 987 by the company ICI; sorbitan glyceryl isostearate, such as the product sold under the name Arlacel 986 by the company ICI, the mixture of sorbitan isostearate and polyglyceryl isostearate (3 mol) sold under the name Arlacel 1690 by the company Uniqema, and mixtures thereof.

The emulsifier may also be chosen from alkylpolyglycosides with an HLB of less than 7, for example those represented by the general formula (VI) below:

 (VI)

in which R represents a branched and/or unsaturated alkyl radical comprising from 14 to 24 carbon atoms, G represents a reduced sugar comprising 5 or 6 carbon atoms, and x is a value ranging from 1 to 10 and preferably from 1 to 4, and G especially denotes glucose, fructose or galactose.

The unsaturated alkyl radical may comprise one or more ethylenic unsaturations, and in particular one or two ethylenic unsaturations.

As alkylpolyglycosides of this type, mention may be made of alkylpolyglucosides (G=glucose in formula (VI)), and especially the compounds of formula (VI) in which R more particularly represents an oleyl radical (unsaturated $C_{18}$ radical) or isostearyl radical (saturated $C_{18}$ radical), G denotes glucose, x is a value ranging from 1 to 2, especially isostearyl glucoside or oleyl glucoside, and mixtures thereof. This alkylpolyglucoside may be used as a mixture with a coemulsifier, more especially with a fatty alcohol and especially a fatty alcohol containing the same fatty chain as that of the alkylpolyglucoside, i.e. comprising from 14 to 24 carbon atoms and containing a branched and/or unsaturated chain, for example isostearyl alcohol when the alkylpolyglucoside is isostearyl glucoside, and oleyl alcohol when the alkylpolyglucoside is oleyl glucoside, optionally in the form of a self-emulsifying composition, as described, for example, in document WO-A-92/06778. Use may be made, for example, of the mixture of isostearyl glucoside and isostearyl alcohol, sold under the name Montanov WO 18 by the company SEPPIC.

Mention may also be made of succinic-terminated polyolefins, for instance esterified succinic-terminated polyisobutylenes and salts thereof, especially the diethanolamine salts, such as the commercial products sold under the names Lubrizol 2724, Lubrizol 2722 and Lubrizol 5603 by the company Lubrizol or the commercial product Chemcinnate 2000.

The preferred emulsifier is Polyglyceryl-3 diisostearate (INCI name) sold under the name Lameform TGI by Cognis.

Hydrophilic Phase

The ink may comprise water in a mass content ranging from 19.9% to 97.9% by weight, preferably ranging from 29.90% to 89.9% by weight and preferentially ranging from 39.9% to 79.9%, relative to the total mass of the composition.

The compound(s) of the hydrophilic phase may have a solubility in water at 25° C. of greater than or equal to 5% by weight.

The compound(s) of the hydrophilic phase are chosen, for example, from $C_5$-$C_6$ monoalcohols, $C_2$-$C_6$ polyols, $C_6$-$C_{10}$ esters, $C_5$-$C_8$ ketones (especially cyclic), $C_6$-$C_7$ aldehydes, $C_3$-$C_8$ cyclic carbonates, $C_3$-$C_8$ cyclic ureas, $C_2$-$C_6$ amino alcohols, $C_3$-$C_6$ diamines, water-miscible amino silicones such as Silicone Quaternium-8 (INCI name) sold, for example, under the name Silsense Q-Plus Silicone by Noveon, PEG-7 amodimethicone (INCI name) sold, for example, under the name Silsense A-21 Silicone by Noveon, and mixtures thereof.

In one embodiment example, the compounds of the hydrophilic phase comprise a mixture of at least two different $C_2$-$C_6$ polyols, especially of at least three different $C_2$-$C_6$ polyols and especially of at least four different $C_2$-$C_6$ polyols.

The hydrophilic phase may comprise one or more hydrophilic organic solvents such as alcohols and especially linear or branched lower monoalcohols containing from 2 to 10 carbon atoms, for instance ethanol, isopropanol or n-propanol, butanol, hexanol and polyols, for instance glycerol, diglycerol, propylene glycol, sorbitol or pentylene glycol, and polyethylene glycols, or alternatively $C_2$ ethers and hydrophilic $C_2$-$C_4$ aldehydes.

Oily Phase

The compound(s) of the oily phase may have a solubility in water at 25° C. of less than 5% by weight.

The compound(s) of the oily phase may be chosen from the oils usually used in cosmetics, which may be chosen from natural or synthetic carbon-based, hydrocarbon-based or fluoro oils, which are optionally branched, alone or as a mixture.

The term "non-volatile oil" means an oil that is capable of remaining on the skin at room temperature and atmospheric pressure for at least one hour, and especially having a non-zero vapour pressure at room temperature (25° C.) and atmospheric pressure, of less than 0.01 mmHg (1.33 Pa).

Mention may be made in particular of non-volatile carbon-based, especially hydrocarbon-based oils of plant, mineral, animal or synthetic origin, such as liquid paraffin (or petroleum jelly), squalane, hydrogenated polyisobutene (Parleam oil), perhydrosqualene, macadamia oil, soybean oil, sweet almond oil, beauty-leaf oil, palm oil, grapeseed oil, sesame oil, corn oil, arara oil, rapeseed oil, sunflower oil, cotton oil, apricot oil, castor oil, avocado oil, jojoba oil, olive oil, cereal germ oil or shea butter oil; linear, branched or cyclic esters containing more than 6 carbon atoms, especially 6 to 30 carbon atoms, such as esters of lanolic acid, of oleic acid, of lauric acid or of stearic acid; esters derived from long-chain acids or alcohols (i.e. containing from 6 to 20 carbon atoms), especially the esters of formula RCOOR' in which R represents a higher fatty acid residue comprising from 7 to 19 carbon atoms and R' represents a hydrocarbon-based chain comprising from 3 to 20 carbon atoms, in particular $C_{12}$-$C_{36}$ esters, such as isopropyl myristate, isopropyl palmitate, butyl stearate, hexyl laurate, diisopropyl adipate, isononyl isononanoate, 2-ethylhexyl palmitate, 2-hexyldecyl laurate, 2-octyldecyl palmitate, 2-octyldodecyl myristate or lactate, bis(2-ethylhexyl) succinate, diisostearyl malate, and glyceryl or diglyceryl triisostearate; higher fatty acids, especially of $C_{14}$-$C_{22}$, such as myristic acid, palmitic acid, stearic acid, behenic acid, oleic acid, linoleic acid, linolenic acid or isostearic acid; higher fatty alcohols, especially of $C_{16}$-$C_{22}$, such as cetanol, oleyl alcohol, linoleyl alcohol or linolenyl alcohol, isostearyl alcohol or octyldodecanol; and mixtures thereof.

Mention may also be made of decanol, dodecanol, octadecanol, liquid fatty acid triglycerides of 4 to 10 carbon atoms such as heptanoic or octanoic acid triglycerides, caprylic/capric acid triglycerides; linear or branched hydrocarbons, of mineral or synthetic origin such as liquid paraffins and derivatives thereof, petroleum jelly, polydecenes and hydrogenated polyisobutene such as Parleam; synthetic esters and ethers especially of fatty acids, for instance purcellin oil, isopropyl myristate, 2-ethylhexyl palmitate, 2-octyldodecyl stearate, 2-octyldodecyl erucate or isostearyl isostearate; hydroxylated esters such as isostearyl lactate, octyl hydroxystearate, octyldodecyl hydroxystearate, diisostearyl malate, triisocetyl citrate or fatty alkyl heptanoates, octanoates and decanoates; polyol esters such as propylene glycol dioctanoate, neopentyl glycol diheptanoate or diethylene glycol diisononanoate; and pentaerythritol esters;

fatty alcohols containing from 12 to 26 carbon atoms, such as octyldodecanol, 2-butyloctanol, 2-hexyldecanol or 2-undecylpentadecanol.

Among the volatile compounds, mention may be made of non-silicone volatile oils, especially $C_8$-$C_{16}$ isoparaffins, such as isododecane, isodecane and isohexadecane.

More preferentially, mention may be made of volatile or non-volatile alkanes that are liquid at room temperature, and more particularly decane, heptane, dodecane, isododecane, isohexadecane, cyclohexane and isodecane, and mixtures thereof.

Among the preferred compounds of the oily phase, examples that may be mentioned include isododecane (boiling point: 180° C.), isopropyl myristate (boiling point: 168° C.), isostearyl alcohol (boiling point: 331° C.), isodecyl neopentanoate (boiling point: 272° C.), isononyl isononanoate (boiling point: 285° C.), oleyl alcohol (boiling point: 315° C.), 2-octyldodecanol (boiling point: 358° C.), isopropyl palmitate (boiling point: 340° C.), isopropyl isostearate (boiling point: 361° C.), and mixtures thereof.

The oil may be present in the ink composition in a content ranging from 2% to 60%, preferably ranging from 2% to 40%, preferably ranging from 15% to 70% and particularly preferably ranging from 2% to 25%, relative to the total mass of the ink.

The oily phase may also comprise substances that are solid at room temperature, such as waxes.

The term "wax" means a lipophilic compound, which is solid at room temperature (25° C.), with a reversible solid/liquid change of state, with a melting point of greater than or equal to 30° C., which may be up to 120° C. By bringing the wax to the liquid state (melting), it is possible to make it miscible with the oils that may be present and to form a microscopically homogeneous mixture, but on returning the temperature of the mixture to room temperature, recrystallization of the wax in the oils of the mixture is obtained. The melting point of the wax may be measured using a differential scanning calorimeter (DSC), for example the calorimeter sold under the name DSC 30 by the company Mettler.

The waxes may be hydrocarbon-based waxes, fluoro waxes and/or silicone waxes, and may be of plant, mineral, animal and/or synthetic origin. In particular, the waxes have a melting point of greater than 25° C. and better still greater than 45° C. As waxes that may be used in the ink, mention may be made of beeswax, carnauba wax or candelilla wax, paraffin, microcrystalline waxes, ceresin or ozokerite, synthetic waxes such as polyethylene waxes or Fischer-Tropsch waxes, silicone waxes such as alkyl or alkoxy dimethicones containing from 16 to 45 carbon atoms.

The nature and amount of the waxes depend on the desired mechanical properties and textures. As a guide, the ink in emulsion form may contain from 0.01% to 30% by weight and better still from 1% to 20% by weight of waxes relative to the total weight of the cosmetic ink.

Additional Compounds

The ink may also comprise additional compounds such as fragrances or preserving agents.

The cosmetic ink may comprise no particulate filler.

In one variant, the cosmetic ink also comprises one or more fillers, especially in a content ranging from 0.01% to 50% by weight, relative to the total weight of the cosmetic ink, preferably ranging from 0.01% to 30% by weight.

The term "fillers" should be understood as meaning colourless or white, mineral or synthetic particles of any shape, which are insoluble in the medium of the ink, irrespective of the temperature at which this ink is manufactured.

These fillers serve especially to modify the rheology or texture of the ink.

The fillers may be mineral or organic and of any shape, platelet-shaped, spherical or oblong, irrespective of the crystallographic form (for example lamellar, cubic, hexagonal, orthorhombic, etc.). Mention may be made of talc, mica, silica, kaolin, polyamide (Nylon®) powder (Orgasol® from Atochem), poly-β-alanine powder and polyethylene powder, tetrafluoroethylene polymer (Teflon®) powder, lauroyllysine, starch, boron nitride, hollow polymer microspheres such as polyvinylidene chloride/acrylonitrile microspheres, for instance Expancel® (Nobel Industrie), acrylic acid copolymer microspheres (Polytrap® from the company Dow Corning) and silicone resin microbeads (for example Tospearls® from Toshiba), elastomeric polyorganosiloxane particles, precipitated calcium carbonate, magnesium carbonate, magnesium hydrogen carbonate, hydroxyapatite, hollow silica microspheres (Silica Beads® from Maprecos), glass or ceramic microcapsules, and metal soaps derived from organic carboxylic acids containing from 8 to 22 carbon atoms and preferably from 12 to 18 carbon atoms, for example zinc stearate, magnesium stearate, lithium stearate, zinc laurate or magnesium myristate.

Needless to say, a person skilled in the art will take care to select this or these optional additional compound(s), and/or the amount thereof, such that the advantageous properties of the colouring ink are not, or are not substantially, adversely affected by the envisaged addition.

The use of an ink in the form of an emulsion or a nanoemulsion also makes it possible to improve the functioning of the printer nozzles by virtue of the physicochemical properties of the emulsion or nanoemulsion.

The invention also makes it possible to use the cosmetic qualities of an emulsion or a nanoemulsion, for example a soft care effect (on the skin or the hair), or even an effect of aiding the penetration of the colouring compounds or of the care active agents, in particular for the skin.

The emulsion or nanoemulsion is advantageous for giving the skin or the hair care benefits, or for facilitating the transfer of intermediary compounds, such as care active agents, including in embodiment examples for which the dyestuff especially comprising water-soluble dyes does not require an emulsion or nanoemulsion.

Another advantage of an emulsion lies in the compartmentation properties that these physicochemical forms allow. For example, compounds that are sparingly compatible may be used. This also makes it possible to combine, if need be, two or even more dyes, one of which is hydrophilic and the other hydrophobic, in the same cartridge. The colour shade obtained is thus refined, and the number of cartridges to be used is reduced while at the same time making it possible to achieve a wide range of colours.

Nanoemulsion

Nanoemulsions are emulsions characterized by a mean size of the droplets of the dispersed phase of the order of a few tens of nanometres. The mean size of the droplets of the discontinuous dispersed phase is, for example, between 10 and 200 nanometres.

In a manner known to those skilled in the art, a nanoemulsion may have an opaque or translucent appearance. The translucent appearance of these emulsions originates from the small size of the droplets of the dispersed phase, this small size being obtained by means of using mechanical energy and especially a high-pressure homogenizer.

The process for preparing a nanoemulsion according to the invention consists, for example, in mixing the aqueous phase and the oily phase, with vigorous stirring, at a temperature ranging from 10° C. to 80° C. and in performing a high-pressure homogenization step at a pressure above $5\times10^7$ Pa.

According to a preferred embodiment of the invention, a further high-pressure homogenization step is then performed at a pressure above $5\times10^7$ Pa.

The high-pressure homogenization is preferably performed at a pressure ranging from $6\times10^7$ to $18\times10^7$ Pa. The shear preferably ranges from $2\times10^6$ s$^{-1}$ to $5\times10^8$ s$^{-1}$ and better still from $1\times10^8$ s$^{-1}$ to $3\times10^8$ s$^{-1}$.

The nanoemulsion in accordance with the invention is preferably prepared at a temperature ranging from 4 to 45° C.

The nanoemulsion according to the invention may have a transparent to blueish appearance.

The transparency of the nanoemulsion according to the invention may have a coefficient of transmittance, measured at 600 nm, ranging from 10% to 90%.

The turbidity of the nanoemulsion according to the invention ranges, for example, from 60 to 400 NTU and preferably from 70 to 300 NTU, the turbidity being measured using a HACH—model 2100 P portable turbidimeter at about 25° C.

The ink may be an O/W nanoemulsion comprising oil globules which have a mean size of less than 100 nm, preferably ranging from 20 to 80 nm and more preferentially from 40 to 60 nm. Reducing the size of the globules makes it possible to convey the active agents better and to promote their penetration into the surface layers of the skin.

The number mean size of the particles may be determined in particular according to the method known as quasi-elastic light scattering. As a machine that may be used for this determination, mention may be made of the Brookhaven brand machine equipped with an SX 200 optical bench (with a 532 nm laser) and a BI 9000 correlator. This machine gives a measurement of the mean diameter by photon correlation spectroscopy (PCS), which makes it possible to determine the number mean diameter from the polydispersity factor, also measured by the machine.

The nanoemulsion may comprise a hydrophilic phase, an oily phase and surfactants as described above.

The nanoemulsion according to the invention is preferably an oil-in-water emulsion comprising an oily phase dispersed in an aqueous phase.

Surfactants

The nanoemulsion, especially the oily phase, may comprise at least one amphiphilic lipid, preferably at least one nonionic amphiphilic lipid.

The nanoemulsion, especially the oily phase, may also comprise an ionic amphiphilic lipid.

The oily phase and the amphiphilic lipid(s) are, for example, present in the ink in a mass content such that the oily phase/amphiphilic lipid(s) mass ratio ranges from 3 to 10 and especially from 2 to 6.

Depending on its nature, more hydrophilic or more lipophilic, the nonionic or ionic amphiphilic lipid may be introduced into the aqueous phase or into the oily phase of the nanoemulsion. The total mass content of nonionic and ionic amphiphilic lipids may preferably range from 0.25% to 150% and preferably from 1% to 10% relative to the total mass of the nanoemulsion.

The nonionic amphiphilic lipids may be present in the nanoemulsion according to the invention in a mass content ranging from 0.2% to 12% by weight, preferably ranging from 0.2% to 8% and preferentially ranging from 0.2% to 6% relative to the total mass of the ink.

When the nanoemulsion contains one or more ionic amphiphilic lipids, they are preferably present in the nanoemulsion of the invention in a mass concentration ranging from 0.01% to 6% and more particularly from 0.2% to 4% relative to the total mass of the nanoemulsion.

The nonionic amphiphilic lipids of the invention are preferentially chosen from:
  silicone surfactants,
  amphiphilic lipids that are liquid at a temperature of less than or equal to 45° C., chosen from esters of at least one polyol of at least one fatty acid containing at least one saturated or unsaturated, linear or branched, and especially unsaturated or branched, $C_8$-$C_{22}$ alkyl chain, the polyol being chosen from the group formed by polyethylene glycol comprising from 1 to 60 ethylene oxide units, sorbitan, glycerol possibly comprising from 2 to 30 ethylene oxide units, and polyglycerols comprising from 2 to 15 glycerol units,
  fatty acid esters of sugars and fatty alkyl ethers of sugars,
  surfactants that are solid at a temperature equal to 45° C., chosen from fatty esters of glycerol, fatty esters of sorbitan and oxyethylenated fatty esters of sorbitan, ethoxylated fatty ethers and ethoxylated fatty esters,
  block copolymers of ethylene oxide (A) and of propylene oxide (B), and mixtures of these surfactants.

The silicone surfactants that may be used according to the invention are silicone compounds comprising at least one oxyethylene —$OCH_2CH_2$— and/or oxypropylene —$OCH_2CH_2CH_2$— chain.

As silicone surfactants that may be used according to the present invention, mention may be made of those described in documents U.S. Pat. Nos. 5,364,633 and 5,411,744.

Preferably, the silicone surfactant used according to the present invention is a compound of formula (VII):

$$R_1-\underset{\underset{CH_3}{|}}{\overset{\overset{CH_3}{|}}{Si}}-O-\left[\underset{\underset{CH_3}{|}}{\overset{\overset{CH_3}{|}}{Si}}-O\right]_A-\left[\underset{\underset{R_2}{|}}{\overset{\overset{CH_3}{|}}{Si}}-O\right]_B-\underset{\underset{CH_3}{|}}{\overset{\overset{CH_3}{|}}{Si}}-R_3 \qquad (VII)$$

in which:
$R_1$, $R_2$ and $R_3$, independently of each other, represent a $C_1$-$C_6$ alkyl radical or a radical —$(CH_2)_x$—$(OCH_2CH_2)_y$—$(OCH_2CH_2CH_2)_z$—$OR_4$, at least one radical $R_1$, $R_2$ or $R_3$ not being an alkyl radical; $R_4$ being a hydrogen, an alkyl radical or an acyl radical;
A is an integer ranging from 0 to 200;
B is an integer ranging from 0 to 50; on condition that A and B are not simultaneously equal to zero;
x is an integer ranging from 1 to 6;
y is an integer ranging from 1 to 30,
z is an integer ranging from 0 to 5.

According to one preferred embodiment of the invention, in the compound of formula (VII), the alkyl radical is a methyl radical, x is an integer ranging from 2 to 6 and y is an integer ranging from 4 to 30.

Examples of silicone surfactants of formula (VII) that may be mentioned include the compounds of formula (VIII):

$$(CH_3)_3SiO-[(CH_3)_2SiO]_A-(CH_3SiO)_B-Si(CH_3)_3 \atop {\overset{|}{(CH_2)_2(OCH_2CH_2)y-OH}} \qquad (VIII)$$

in which A is an integer ranging from 20 to 105, B is an integer ranging from 2 to 10 and y is an integer ranging from 10 to 20.

Examples of silicone surfactants of formula (VII) that may also be mentioned include the compounds of formula (IX):

in which A' and y are integers ranging from 10 to 20.

Silicone surfactants that may especially be used are those sold by the company Dow Corning under the names DC 5329, DC 7439-146, DC 2-5695 and Q4-3667. The compounds DC 5329, DC 7439-146 and DC 2-5695 are compounds of formula (VIII) in which, respectively, A is 22, B is 2 and y is 12; A is 103, B is 10 and y is 12; A is 27, B is 3 and y is 12. The compound Q4-3667 is a compound of formula (IX) in which A is 15 and y is 13.

The amphiphilic lipids that are liquid at a temperature of less than or equal to 45° C. may be chosen especially from:
polyethylene glycol isostearate of molar weight 400 (CTFA name: PEG-8 isostearate), sold under the name Prisorine 3644 by the company Uniqema;
diglyceryl isostearate, sold by the company Solvay;
polyglyceryl laurate comprising 2 glycerol units (polyglyceryl-2 laurate), sold under the name diglycerin monolaurate by the company Solvay;
sorbitan oleate, sold under the name Span 80 by the company ICI;
sorbitan isostearate, sold under the name Nikkol SI 10R by the company Nikko;
α-butylglucoside cocoate or α-butylglucoside caprate sold by the company Ulice.

The fatty acid esters of sugars that may be used as nonionic amphiphilic lipids in the nanoemulsion according to the invention are preferably solid at a temperature of less than or equal to 45° C. and may be chosen especially from the group comprising esters or mixtures of esters of $C_8$-$C_{22}$ fatty acids and of sucrose, maltose, glucose or fructose, and esters or mixtures of esters of $C_{14}$-$C_{22}$ fatty acids and of methylglucose.

The $C_8$-$C_{22}$ or $C_{14}$-$C_{22}$ fatty acids forming the fatty unit of the esters that may be used in the nanoemulsion of the invention comprise a saturated or unsaturated linear alkyl chain, of 8 to 22 or of 14 to 22 carbon atoms, respectively. The fatty unit of the esters may be chosen especially from stearates, behenates, arachidonates, palmitates, myristates, laurates and caprates, and mixtures thereof. Stearates are preferably used.

Examples of esters or mixtures of esters of fatty acid and of sucrose, maltose, glucose or fructose that may be mentioned include sucrose monostearate, sucrose distearate and sucrose tristearate, and mixtures thereof, such as the products sold by the company Croda under the name Crodesta F50, F70, F110 and F160, respectively having an HLB (Hydrophilic-Lipophilic Balance) of 5, 7, 11 and 16; and an example of esters or mixtures of esters of fatty acid and of methylglucose that may be mentioned is methylglucose polyglyceryl-3 distearate, sold by the company Goldschmidt under the name Tegocare 450. Mention may also be made of monoesters of glucose or of maltose such as methyl O-hexadecanoyl-6-D-glucoside and O-hexadecanoyl-6-D-maltoside.

The sugar fatty alcohol ethers that may be used as nonionic amphiphilic lipids in the nanoemulsion according to the invention are preferably solid at a temperature of less than or equal to 45° C. and may be chosen especially from the group comprising ethers or mixtures of ethers of $C_8$-$C_{22}$ fatty alcohol and of glucose, maltose, sucrose or fructose, and ethers or mixtures of ethers of $C_{14}$-$C_{22}$ fatty alcohol and of methylglucose. They are especially alkylpolyglucosides.

The $C_8$-$C_{22}$ or $C_{14}$-$C_{22}$ fatty alcohols forming the fatty unit of the ethers that may be used in the nanoemulsion of the invention comprise a saturated or unsaturated linear alkyl chain, of 8 to 22 or of 14 to 22 carbon atoms, respectively. The fatty unit of the ethers may be chosen especially from decyl, cetyl, behenyl, arachidyl, stearyl, palmityl, myristyl, lauryl, capryl and hexadecanoyl units, and mixtures thereof such as cetearyl.

As examples of sugar fatty alcohol ethers that may be used in the invention, mention may be made of alkylpolyglucosides such as decyl glucoside and lauryl glucoside sold, for example, by the company Henkel under the respective names Plantaren 2000 and Plantaren 1200, cetostearyl glucoside optionally as a mixture with cetostearyl alcohol, sold, for example, under the name Montanov 68 by the company SEPPIC, under the name Tegocare CG90 by the company Goldschmidt and under the name Emulgade KE3302 by the company Henkel, and also arachidyl glucoside, for example in the form of the mixture of arachidyl and behenyl alcohols and of arachidyl glucoside, sold under the name Montanov 202 by the company SEPPIC.

Sucrose monostearate, sucrose distearate, sucrose tristearate and mixtures thereof, methylglucose polyglyceryl-3 distearate and alkylpolyglucosides are more particularly used as nonionic amphiphilic lipid of this type.

The fatty esters of glycerol that may be used as nonionic amphiphilic lipids in the nanoemulsion according to the invention, which are solid at a temperature equal to 45° C., may be chosen especially from the group comprising the esters formed from at least one acid comprising a saturated linear alkyl chain containing from 16 to 22 carbon atoms and from 1 to 10 glycerol units. One or more of these fatty esters of glycerol may be used in the nanoemulsion of the invention.

These esters may be chosen especially from stearates, behenates, arachidates and palmitates, and mixtures thereof. Stearates and palmitates are preferably used.

As examples of surfactants that may be used in the nanoemulsion according to the invention, mention may be made of decaglyceryl monostearate, distearate, tristearate and pentastearate (10 glycerol units) (CTFA names: polyglyceryl-10 stearate, polyglyceryl-10 distearate, polyglyceryl-10 tristearate and polyglyceryl-10 pentastearate), such as the products sold under the respective names Nikkol Decaglyn 1-S, 2-S, 3-S and 5-S by the company Nikko and diglyceryl monostearate (CTFA name: polyglyceryl-2 stearate), such as the product sold by the company Nikko under the name Nikkol DGMS.

The fatty esters of sorbitan that may be used as nonionic amphiphilic lipids in the nanoemulsion according to the invention, which are solid at a temperature of less than or equal to 45° C., are chosen especially from the group comprising esters of $C_{16}$-$C_{22}$ fatty acid and of sorbitan and oxyethylenated esters of $C_{16}$-$C_{22}$ fatty acid and of sorbitan. They are formed from at least one fatty acid comprising at least one saturated linear alkyl chain containing, respectively, from 16 to 22 carbon atoms and from sorbitol or ethoxylated sorbitol. The oxyethylenated esters generally comprise from 1 to 100 ethylene oxide units and preferably from 2 to 40 ethylene oxide (EO) units.

These esters may be chosen especially from stearates, behenates, arachidates and palmitates, and mixtures thereof. Stearates and palmitates are preferably used.

As examples of fatty esters of sorbitan and of oxyethylenated fatty esters of sorbitan that may be used in the nanoemulsion of the invention, mention may be made of sorbitan monostearate (CTFA name: sorbitan stearate) sold by the company ICI under the names Span 60, sorbitan monopalmitate (CTFA name: sorbitan palmitate) sold by the company ICI under the name Span 40, and sorbitan 20 EO tristearate (CTFA name: polysorbate 65) sold by the company ICI under the name Tween 65.

The ethoxylated fatty ethers that are solid at a temperature less than or equal to 45° C., which may be used as nonionic amphiphilic lipids in the nanoemulsion according to the invention, are preferably ethers formed from 1 to 100 ethylene oxide units and from at least one fatty alcohol chain containing from 16 to 22 carbon atoms. The fatty chain of the ethers may be chosen especially from behenyl, arachidyl, stearyl and cetyl units, and mixtures thereof, such as cetearyl. Examples of ethoxylated fatty ethers that may be mentioned include behenyl alcohol ethers comprising 5, 10, 20 and 30 ethylene oxide units (CTFA names: beheneth-5, beheneth-10, beheneth-20, beheneth-30), such as the products sold under the names Nikkol BB5, BB10, BB20 and BB30 by the company Nikko, and stearyl alcohol ether comprising 2 ethylene oxide units (CTFA name: steareth-2), such as the product sold under the name Brij 72 by the company ICI.

The ethoxylated fatty esters that are solid at a temperature less than or equal to 45° C., which may be used as nonionic amphiphilic lipids in the nanoemulsion according to the invention are esters formed from 1 to 100 ethylene oxide units and from at least one fatty acid chain containing from 16 to 22 carbon atoms. The fatty chain of the esters may be chosen especially from stearate, behenate, arachidate and palmitate units, and mixtures thereof. Examples of ethoxylated fatty esters that may be mentioned include stearic acid ester comprising 40 ethylene oxide units, such as the product sold under the name Myrj 52 (CTFA name: PEG-40 stearate) by the company ICI, and also the behenic acid ester comprising 8 ethylene oxide units (CTFA name: PEG-8 behenate), such as the product sold under the name Compritol HD5 ATO by the company Gattefosst.

The block copolymers of ethylene oxide and of propylene oxide that may be used as nonionic amphiphilic lipids in the nanoemulsion according to the invention may be chosen especially from the block copolymers of formula (X):

HO(C$_2$H$_4$O)x(C$_3$H$_6$O)y(C$_2$H$_4$O)zH    (X)

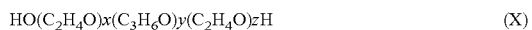

in which x, y and z are integers such that x+z ranges from 2 to 100 and y ranges from 14 to 60,
and mixtures thereof, and more particularly from the block copolymers of formula (X) with an HLB ranging from 2 to 16.

These block copolymers may be chosen especially from poloxamers and especially from poloxamer 231, such as the product sold by the company ICI under the name Pluronic L81 of formula (X) with x=z=6, y=39 (HLB 2); poloxamer 282, such as the product sold by the company ICI under the name Pluronic L92 of formula (V) with x=z=10, y=47 (HLB 6); and poloxamer 124, such as the product sold by the company ICI under the name Pluronic L44 of formula (X) with x=z=11, y=21 (HLB 16).

Nonionic amphiphilic lipids that may also be mentioned include the nonionic surfactant mixtures described in document EP-A-705 593, which is incorporated herein for reference.

Among the nonionic amphiphilic lipids that may be used in particular are:
PEG 400 isostearate or PEG-8 isostearate (comprising 8 mol of ethylene oxide),
diglyceryl isostearate,
polyglyceryl monolaurate comprising 2 glycerol units, and polyglyceryl stearates comprising 10 glycerol units,
sorbitan oleate,
sorbitan isostearate,
and mixtures thereof.

According to a particular embodiment of the invention, the nanoemulsion of the invention may also contain one or more ionic amphiphilic lipids, in particular one or more anionic or cationic lipids, other than the nonionic amphiphilic lipids described previously. Their addition may further improve the stability of the dispersion.

Thus, the anionic amphiphilic lipids that may be used in the nanoemulsions of the invention are preferably chosen from:
alkali metal salts of dicetyl and dimyristyl phosphate.
alkali metal salts of cholesteryl sulfate,
alkali metal salts of cholesteryl phosphate,
lipoamino acids and salts thereof such as monosodium and disodium acylglutamates, for instance the disodium salt of N-stearoyl-L-glutamic acid sold under the name Acylglutamate HS21 by the company Ajinomoto,
the sodium salts of phosphatidic acid,
phospholipids,
alkylsulfonic derivatives especially of formula (XI):

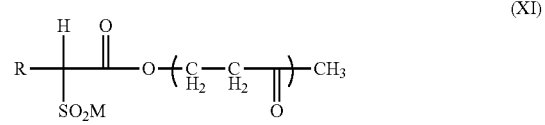

(XI)

in which R represents $C_{16}$-$C_{22}$ alkyl radicals, in particular $C_{16}H_{33}$ and $C_{18}H_{37}$ radicals, taken as a mixture or separately, and M is an alkali metal or alkaline-earth metal such as sodium; and mixtures thereof.

The cationic amphiphilic lipids that may be used in the nanoemulsions of the invention are preferably chosen from the group formed by quaternary ammonium salts and fatty amines, and salts thereof.

Examples of quaternary ammonium salts include:
those that have the general formula (XII) below:

(XII)

in which:
the radicals $R_1$ to $R_4$, which may be identical or different, represent a linear or branched aliphatic radical containing from 1 to 30 carbon atoms, or an aromatic radical such as aryl or alkylaryl. The aliphatic radicals may comprise heteroatoms especially such as oxygen, nitrogen, sulfur and halogens. The aliphatic radicals are chosen, for example, from alkyl, alkoxy, polyoxy($C_2$-$C_6$)alkylene, alkylamide, ($C_{12}$-$C_{22}$)alkylamido($C_2$-$C_6$)alkyl, ($C_{12}$-$C_{22}$)alkylacetate and hydroxyalkyl radicals, comprising from about 1 to 30 carbon atoms; X is an anion chosen from the group of halides, phosphates, acetates, lactates, ($C_2$-$C_6$)alkyl sulfates and alkyl or alkylaryl sulfonates, quaternary ammonium salts of imidazoline, for instance that of formula (XIII) below:

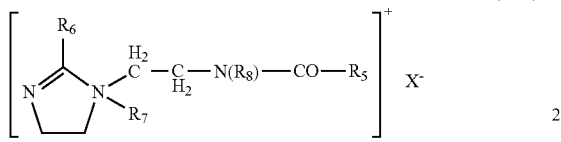

(XIII)

in which:
$R_5$ represents an alkenyl or alkyl radical comprising from 8 to 30 carbon atoms, for example derived from tallow fatty acids,
$R_6$ represents a hydrogen atom, a $C_1$-$C_4$ alkyl radical or an alkenyl or alkyl radical comprising from 8 to 30 carbon atoms,
$R_7$ represents a $C_1$-$C_4$ alkyl radical, $R_8$ represents a hydrogen atom or a $C_1$-$C_4$ alkyl radical,
X is an anion chosen from the group of halides, phosphates, acetates, lactates, alkyl sulfates and alkyl- or alkylaryl-sulfonates.
Preferably, $R_5$ and $R_6$ denote a mixture of alkenyl or alkyl radicals containing from 12 to 21 carbon atoms, for example tallow fatty acid derivatives, and $R_7$ denotes methyl, $R_8$ denotes hydrogen.
Such a product is sold, for example, under the name Rewoquat W 75 by the company Rewo, Among the quaternary ammonium salts of formula (XIII), preference is firstly given to tetraalkylammonium chlorides, for instance dialkyldimethylammonium or alkyltrimethylammonium chlorides in which the alkyl radical comprises approximately from 12 to 22 carbon atoms, in particular behenyltrimethylammonium, distearyldimethylammonium, cetyltrimethylammonium, and benzyldimethylstearylammonium chlorides, or else, secondly, to stearamidopropyldimethyl(myristyl acetate)ammonium chloride, which is sold under the name Ceraphyl® 70 by the company Van Dyk. Behenyltrimethylammonium chloride is the most particularly preferred quaternary ammonium salt, the quaternary diammonium salts of formula (XIV):

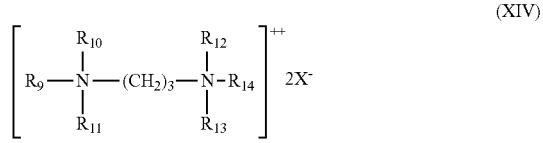

(XIV)

in which:
$R_9$ denotes an aliphatic radical comprising from about 16 to 30 carbon atoms,
$R_{10}$, $R_{11}$, $R_{12}$, $R_{13}$ and $R_{14}$, which may be identical or different, are chosen from hydrogen and an alkyl radical comprising from 1 to 4 carbon atoms, and X is an anion chosen from the group of halides, acetates, phosphates, nitrates and methyl sulfates.

Such quaternary diammonium salts in particular comprise propanetallowdiammonium dichloride, quaternary ammonium salts containing at least one ester function. The quaternary ammonium salts containing at least one ester function that may be used according to the invention are, for example, those of formula (XV) below:

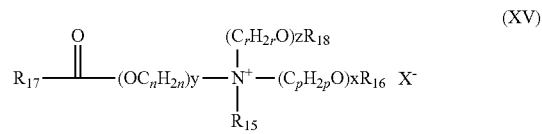

(XV)

in which:
$R_{15}$ is selected from $C_1$-$C_6$ alkyl radicals and $C_1$-$C_6$ hydroxyalkyl or dihydroxyalkyl radicals;
$R_{16}$ is chosen from:
the radical

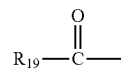

linear or branched, saturated or unsaturated $C_1$-$C_{22}$ hydrocarbon-based radicals $R_{20}$,
a hydrogen atom,
$R_{18}$ is selected from:
the radical

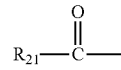

linear or branched, saturated or unsaturated $C_1$-$C_6$ hydrocarbon-based radicals $R_{22}$,
a hydrogen atom,
$R_{17}$, $R_{19}$ and $R_{21}$, which may be identical or different, are chosen from linear or branched, saturated or unsaturated $C_7$-$C_{21}$ hydrocarbon-based radicals;
n, p and r, which may be identical or different, are integers ranging from 2 to 6;
y is an integer ranging from 1 to 10;
x and z, which may be identical or different, are integers ranging from 0 to 10;
$X^-$ is a simple or complex, organic or mineral anion;
with the proviso that the sum x+y+z is from 1 to 15, that when x is 0, then $R_{16}$ denotes $R_{20}$ and that when z is 0, then $R_{18}$ denotes $R_{22}$.
The alkyl radicals $R_{15}$ may be linear or branched, and more particularly linear.
Preferably $R_{15}$ denotes a methyl, ethyl, hydroxyethyl or dihydroxypropyl radical, and more particularly a methyl or ethyl radical.
Advantageously, the sum x+y+z is from 1 to 10.
When $R_{16}$ is a hydrocarbon-based radical $R_{20}$, it may be long and may contain from 12 to 22 carbon atoms, or may be short and may contain from 1 to 3 carbon atoms.
When $R_{18}$ is a hydrocarbon-based radical $R_{22}$, it preferably contains 1 to 3 carbon atoms.

Advantageously, $R_{17}$, $R_{19}$ and $R_{21}$, which may be identical or different, are chosen from linear or branched, saturated or unsaturated $C_{11}$-$C_{21}$ hydrocarbon-based radicals, and more particularly from linear or branched, saturated or unsaturated $C_{11}$-$C_{21}$ alkyl and alkenyl radicals.

Preferably, x and z, which may be identical or different, are equal to 0 or 1.

Advantageously, y is equal to 1.

n, p and r, which may be identical or different, are preferably 2 or 3 and even more particularly are equal to 2.

In formula (XV), the anion $X^-$ is preferably a halide (chloride, bromide or iodide) or an alkyl sulfate, more particularly methyl sulfate. However, it is possible to use methanesulfonate, phosphate, nitrate, tosylate, an anion derived from an organic acid, such as acetate or lactate, or any other anion that is compatible with the ammonium containing an ester function. The anion $X^-$ is even more particularly chloride or methyl sulfate.

Use is made more particularly of the ammonium salts of formula (XV) in which:
  $R_{15}$ denotes a methyl or ethyl radical;
  x and y are equal to 1;
  z is equal to 0 or 1;
  n, p and r are equal to 2;
  $R_{16}$ is chosen from:
  the radical

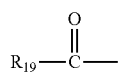

methyl, ethyl or $C_{14}$-$C_{22}$ hydrocarbon-based radicals;
a hydrogen atom;
$R_{18}$ is selected from:
the radical

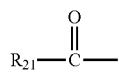

a hydrogen atom;
$R_{17}$, $R_{19}$ and $R_{21}$, which may be identical or different, are chosen from linear or branched, saturated or unsaturated $C_{13}$-$C_{17}$ hydrocarbon-based radicals and preferably from linear or branched, saturated or unsaturated $C_{13}$-$C_{17}$ alkyl and alkenyl radicals.

The hydrocarbon-based radicals are advantageously linear.

Examples of compounds of formula (XV) that may be mentioned include the diacyloxyethyldimethylammonium, diacyloxyethylhydroxyethylmethylammonium, mono-acyloxyethyldihydroxyethylmethylammonium, triacyloxyethylmethylammonium and monoacyloxyethylhydroxyethyldimethylammonium salts (chloride or methyl sulfate in particular), and mixtures thereof. The acyl radicals preferably contain 14 to 18 carbon atoms and are obtained more particularly from a plant oil such as palm oil or sunflower oil. When the compound contains several acyl radicals, these radicals may be identical or different. These products are obtained, for example, by direct esterification of triethanolamine, triisopropanolamine, an alkyldiethanolamine or an alkyldiisopropanolamine, which are optionally oxyalkylenated, with fatty acids or with fatty acid mixtures of plant or animal origin, or by transesterification of the methyl esters thereof. This esterification is followed by a quaternization using an alkylating agent such as an alkyl halide (preferably a methyl or ethyl halide), a dialkyl sulfate (preferably dimethyl or diethyl sulfate), methyl methanesulfonate, methyl para-toluenesulfonate, glycol chlorohydrin or glycerol chlorohydrin.

Such compounds are sold, for example, under the names Dehyquart by the company Henkel, Stepanquat by the company Stepan, Noxamium by the company CECA or Rewoquat WE 18 by the company Rewo-Witco.

When it contains ammonium salts, the ink according to the invention preferably contains a mixture of quaternary ammonium mono-, di- and triester salts with a weight majority of diester salts.

Examples of mixtures of ammonium salts that may be used include the mixture containing mass proportions of 15% to 30% of acyloxyethyldihydroxyethylmethylammonium methyl sulfate, 45% to 60% of diacyloxyethylhydroxyethylmethylammonium methyl sulfate and 15% to 30% of triacyloxyethylmethylammonium methyl sulfate, the acyl radicals containing from 14 to 18 carbon atoms and being derived from optionally partially hydrogenated palm oil.

Use may also be made of the ammonium salts containing at least one ester function that are described in patents U.S. Pat. Nos. 4,874,554 and 4,137,180.

Oily Phase of the Nanoemulsion

The oily phase of the nanoemulsion according to the invention may comprise at least one oil.

The oils that may be used in the nanoemulsion of the invention are preferentially chosen from the group formed by:
  oils of animal or plant origin, formed by fatty acid esters of polyols, in particular liquid triglycerides, for example sunflower oil, corn oil, soybean oil, avocado oil, jojoba oil, marrow oil, grapeseed oil, sesame oil, hazelnut oil, fish oils, glyceryl tricaprocaprylate, or plant or animal oils of formula $R_9COOR_{10}$ in which $R_9$ represents a higher fatty acid residue comprising from 7 to 29 carbon atoms and $R_{10}$ represents a linear or branched hydrocarbon-based chain containing from 3 to 30 carbon atoms, in particular alkyl or alkenyl, for example purcellin oil or liquid jojoba wax;
  natural or synthetic essential oils, for instance eucalyptus oil, hybrid lavender oil, lavender oil, vetiver oil, litsea cubeba oil, lemon oil, sandalwood oil, rosemary oil, camomile oil, savory oil, nutmeg oil, cinnamon oil, hyssop oil, caraway oil, orange oil, geraniol oil, cade oil and bergamot oil;
  synthetic oils such as Parleam oil, polyolefins and liquid carboxylic acid esters;
  mineral oils such as hexa decane, isohexadecane and liquid paraffin;
  halogenated oils, especially fluorocarbons such as fluoroamines, for example perfluorotributylamine, fluoro hydrocarbons, for example perfluorodecahydronaphthalene, fluoro esters and fluoro ethers;
  volatile or non-volatile silicone oils.

The polyolefins that may be used as synthetic oils are in particular poly-α-olefins and more particularly those of hydrogenated or non-hydrogenated polybutene type, and preferably hydrogenated or non-hydrogenated polyisobutene.

The liquid carboxylic acid esters that may be used as synthetic oils may be mono-, di-, tri- or tetracarboxylic acid esters. The total carbon number of the esters is generally greater than or equal to 10 and preferably less than 100 and more particularly less than 80. They are especially monoesters of saturated or unsaturated, linear or branched $C_1$-$C_{26}$ aliphatic acids and of saturated or unsaturated, linear or branched $C_1$-$C_{26}$ aliphatic alcohols, the total carbon number of the esters being generally greater than or equal to 10. Esters of $C_4$-$C_{22}$ dicarboxylic or tricarboxylic acids and of $C_1$-$C_{22}$ alcohols and esters of mono-, di- or tricarboxylic acids and of $C_2$-$C_{26}$ di-, tri-, tetra- or pentahydroxy alcohols may also be used.

Among the esters mentioned above, it is preferred to use alkyl palmitates such as ethyl palmitate, isopropyl palmitate, 2-ethylhexyl palmitate or 2-octyldecyl palmitate; alkyl myristates such as isopropyl myristate, butyl myristate, cetyl myristate or 2-octyldodecyl myristate; alkyl stearates such as hexyl stearate, butyl stearate or isobutyl stearate; alkyl malates such as dioctyl malate, alkyl laurates such as hexyl laurate and 2-hexyldecyl laurate; isononyl isononanoate; or cetyl octanoate.

Advantageously, the nanoemulsion according to the invention contains at least one oil with a molecular mass, expressed in grams/mol, of greater than or equal to 400, especially ranging from 400 to 10 000, better still ranging from 400 to 5000 or alternatively ranging from 400 to 5000. The oils of molecular mass greater than or equal to 400 may be chosen from oils of animal or plant origin, mineral oils, synthetic oils and silicone oils, and mixtures thereof. As oils of this type, examples that may be mentioned include isocetyl palmitate, isocetyl stearate, avocado oil and jojoba oil.

The nanoemulsion in accordance with the invention comprises, for example, a mass amount of oily phase, oil and other fatty substances, besides the amphiphilic lipid(s), preferably ranging from 2% to 40%, more particularly from 4% to 30% and preferentially from 4% to 20% relative to the total mass of the nanoemulsion.

Preferably, the nanoemulsion comprises an oily phase comprising a proportion of oil(s) with a molecular mass of greater than or equal to 400 representing at least 40% by mass of the oily phase.

The oily phase and the amphiphilic lipids (nonionic and ionic amphiphilic agents) are preferably present in the nanoemulsion according to the invention in a mass ratio of the amount of oily phase to the mass of amphiphilic lipids ranging from 3 to 10 and preferentially ranging from 3 to 6. The term "amount of oily phase" means herein the total amount of constituents of this oily phase apart from the amphiphilic lipid(s).

The nanoemulsion in accordance with the present invention may contain solvents, especially to improve, if necessary, the transparency of the composition.

These solvents are preferably chosen from the group formed by:
$C_1$-$C_8$ lower alcohols, such as ethanol;
glycols such as glycerol, propylene glycol, 1,3-butylene glycol and dipropylene glycol, and polyethylene glycols comprising from 4 to 16 and preferably from 8 to 12 ethylene oxide units;
sugars such as glucose, fructose, maltose, lactose or sucrose.

These solvents may be used as a mixture. When they are present in the nanoemulsion of the invention, they may be used at the mass concentrations preferably ranging from 0.01% to 30% relative to the total mass of the nanoemulsion, and better still from 5% to 20% relative to the total mass of the nanoemulsion.

The mass amount of alcohol(s) and/or of sugar(s) preferably ranges from 5% to 20% relative to the total mass of the nanoemulsion and the mass amount of glycol(s) preferably ranges from 5% to 15% relative to the total mass of the nanoemulsion.

According to another aspect, the present invention relates to a device for applying a cosmetic ink by transfer onto human keratin materials, comprising:
a substrate having at least one transfer surface, and
a coat of cosmetic ink borne by the transfer surface and obtained by printing using at least one digital printer, the cosmetic ink being intended to be applied by transfer onto the keratin materials, the ink of the coat being in the form of an emulsion or at least capable of reforming an emulsion in the presence of water.

Between the printing and the transfer onto the keratin materials, when the water of the ink evaporates, the physicochemical structure of the ink changes and the emulsion form is lost. In the presence of water, the structures of the emulsion may reform.

In one variant, the cosmetic ink present on the device is not entirely dry when borne by the surface and before application to the keratin materials after a time of 15 minutes after printing, especially after a time of 24 hours and better still after a time of seven days at 25° C., kept in contact with the air and a normal hygrometry of 55% relative humidity.

The application of an ink that is not entirely dry onto the keratin materials facilitates the transfer of the ink.

All or part of the ink may be in fluid form when borne by the transfer surface immediately before application to the keratin materials.

In a particularly preferred manner, the coat of ink is capable of transferring onto the keratin materials without addition of an intermediary fluid compound, especially a liquid. In other words, the ink may transfer onto the keratin materials by simple contact of the area intended to be made up with the said ink, without it being necessary to apply an intermediary liquid intended to improve the transfer of the ink, as in the case of decal transfers.

The coat of cosmetic ink obtained by printing may be deposited onto the transfer surface by printing in the form of dots and/or of raster lines, so as to form a halftone image, for example a monochromatic or polychromatic image.

The pattern formed by the cosmetic ink printed on the transfer surface may be of any type.

This pattern may reproduce the appearance of relief and/or colour heterogeneities of the skin, for example freckles or a mole.

The pattern formed by the colouring ink borne by the transfer surface may be coloured when observed under white light in the visible region (400 nm-800 nm). As a variant, the pattern is colourless under white light in the visible region, but may appear coloured when submitted to a chemical and/or energy stimulus, such as exposure to UV (365 nm-400 nm), for example when the colouring ink contains a photochromic or fluorescent dyestuff.

Substrate

In one embodiment example, the substrate used in the invention comprises at least one translucent or transparent area.

The translucent or transparent area allows a user to see through the substrate and thus to visualize more easily the surface to be made up and/or treated before transferring the cosmetic ink. The presence of a translucent or transparent area thus advantageously contributes towards facilitating the production of a precise makeup result on the keratin materials.

The translucent or transparent area of the substrate can be totally or partly superposed with the layer of cosmetic ink, and especially may overlap with it.

The layer of cosmetic ink may be superposed in its entirety on the translucent or transparent area of the substrate. As a variant, only part of the layer of cosmetic ink is superposed on the transparent area of the substrate.

The substrate may be made of a transparent or translucent material. In this case, the translucent or transparent area extends over the entire surface of the substrate.

The substrate may comprise a material in sheet form, especially a transparent material.

The substrate is preferentially based on a non-absorbent material, for example a plastic film. The substrate is advantageously non-porous, at least on the face intended to receive the print.

The transfer surface may retain the cosmetic ink by capillary action.

The transfer surface may or may not be planar.

In one embodiment example, the substrate comprises an indication regarding the nature of the keratin materials intended to be made up with the cosmetic ink. This indication may be printed with the same ink or otherwise as that intended to be transferred.

The transfer surface of the substrate may be defined by all or part of: the outer surface of an applicator roller, the surface of an applicator pad, an element in sheet form, a patch, the surface of a porous foam, especially a sponge or a wipe, a coarse brush, a fine brush or a flocked tip.

The transfer surface is defined, for example, by all or part of the surface of a deformable sheet mounted on the surface of an applicator roller.

The transfer surface may be elastically deformable. Thus, in a first configuration, the transfer surface may be flat, and, in a second configuration, the transfer surface may be incurved, for example so as to take the shape of the keratin materials to be made up.

In one embodiment example, the transfer surface is detachable from a part of the substrate.

The substrate may be reusable.

According to another of its aspects, the present invention relates to a cosmetic assembly comprising, in the same packaging, a plurality of devices according to the invention, the devices differing by the chemical nature of the cosmetic ink that they bear and/or by the pattern thereby formed and/or by the form of the transfer surface intended to engage with the keratin materials.

The present invention also relates to a process for making up or caring for human keratin materials, comprising the step consisting in applying to the keratin materials the cosmetic ink present on a device according to the invention, the cosmetic ink especially being applied to the nails, the lips, the hair or to a skin surface, for example the scalp.

Advantageously, the process may be used for applying to the hair or the scalp a cosmetic ink with a hair effect which is in emulsion form.

Advantageously, the cosmetic ink is not entirely dry on the substrate when it is applied to the keratin materials. The cosmetic ink may be in fluid form when it is applied to the keratin materials.

All or part of the cosmetic ink borne by the transfer surface may be applied by transfer to the keratin materials.

In one embodiment illustration, at least 25%, especially 50%, especially 75% and especially substantially all of the coat of cosmetic ink initially present on the transfer surface is preferably applied by transfer to the keratin materials.

The transfer is, for example, from about 50% (evaluated visually) without addition of an intermediary fluid compound.

In one embodiment example, the application of the cosmetic ink is performed by application with pressure of the transfer surface onto the keratin materials.

The application of the cosmetic ink onto the surface to be treated may be performed without rubbing.

In one embodiment example according to the invention, the process also comprises a step of finishing the makeup obtained on the keratin materials, for example so as to attenuate the demarcations between a made-up area and an area not made up. The finishing of the makeup obtained may comprise a step of spreading the cosmetic ink to produce shading-off, for example.

The user may perform finishing before and/or after the transfer of the cosmetic ink onto the keratin materials.

In one embodiment example, the process thus comprises a step of finishing the pattern formed with the ink borne by the transfer surface and/or a step of finishing the makeup obtained on the keratin materials, so as to attenuate the demarcations between a made-up area and an area not made up, the finishing being performed, for example, by exerting friction on only a part of the transferred pattern, for example on its upper part in the case of a pattern applied to the eyelid.

Advantageously, the area of keratin materials intended to receive the ink has not been pretreated at the time of application of the ink.

In one embodiment example, the keratin materials intended to be coated with the cosmetic ink have not been covered, before application of the cosmetic ink, with an intermediary fluid compound intended to improve the transfer of the cosmetic ink and/or the process lacks a step of addition to the cosmetic ink borne by the transfer surface of an intermediary fluid compound intended to improve the transfer.

As a variant, the area of keratin materials intended to be coated with the cosmetic ink has been covered, before application of the ink, with an intermediary fluid compound, especially water or a solvent (for example a water/ethanol mixture; ethanol, an alkane such as isododecane, this list being non-limiting), making it possible to improve the transfer of the ink and/or an intermediary fluid compound intended to improve the transfer has been added to the ink borne by the transfer surface before its application to the keratin materials.

In one embodiment example, the addition of the intermediary fluid compound for improving the transfer of the cosmetic ink makes it possible only to fluidize all or part of the cosmetic ink and not, for example, to dissolve the substrate of the makeup device and/or a layer of adhesive.

The intermediary compound may be added to the cosmetic ink by any known means, especially by spraying.

The intermediary compound is preferably added to the compound(s) before the application of the cosmetic ink to the keratin materials, while the cosmetic ink is still borne by the surface.

According to yet another aspect, the present invention relates to a cosmetic assembly for performing a process for manufacturing a device for applying a cosmetic product according to the invention, comprising, in the same packaging:
  a) a printer cartridge comprising a cosmetic ink in the form of an oil-in-water (O/W) or water-in-oil (W/O) emulsion, which is liquid at 20° C., and
  b) a transfer surface intended to be printed with the cosmetic ink.

DESCRIPTION OF THE FIGURES

The invention may be understood more clearly on reading the following description of non-limiting implementation examples thereof, and on examining the attached drawing, in which:

FIG. 1 shows an example of a makeup device manufactured via a process according to the invention, FIG. 2 is a section along II-II of the makeup device of FIG. 1, FIGS. 3 to 5 represent different steps of an example of a makeup process according to the invention, FIGS. 6 and 7 represent examples of cosmetic assemblies according to the invention.

FIGS. 1 and 2 show a makeup device 1 according to the invention, comprising a substrate 2 whose front side defines a transfer surface 3. The device 1 may, as illustrated, have only one face defining the transfer surface 3, bearing a coat of cosmetic ink 4 according to the invention.

Figure 8:
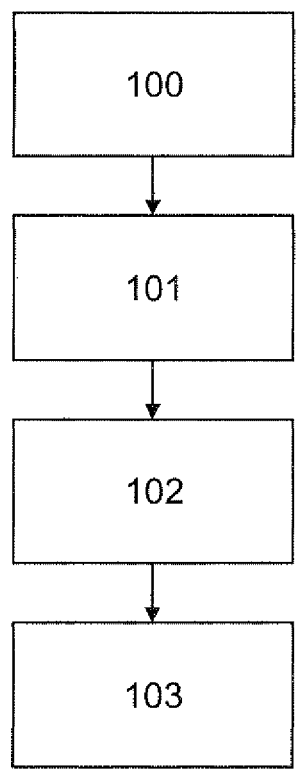
FIG. 8 is a block diagram illustrating the various steps of a process for manufacturing a makeup device according to the invention.

In one variant, not shown, two transfer surfaces 3 are defined by the two opposite faces of the substrate 2. In this case, these surfaces may bear different coats of cosmetic ink, these coats possibly differing by their nature and/or by the pattern formed by the ink.

In the device 1 illustrated in FIGS. 1 and 2, the coat of cosmetic ink 4 borne by the transfer surface 3 was deposited by printing using a digital printer, which deposits the ink spots in correspondence with the pixels of an image to be reproduced. The printing was performed with at least one cosmetic ink that is liquid at a temperature of 20° C. and that is in the form of an oil-in-water (O/W) or water-in-oil (W/O) emulsion comprising a dyestuff.

The coat of cosmetic ink 4 may comprise several different cosmetic inks, as detailed previously.

The coat 4 may form any type of pattern, for example in the form of a heart as illustrated.

The substrate 2 may have at least one non-opaque area 5, which is transparent or translucent, and which may totally or partly be superposed with the coat 4. The transparent area 5 allows the user to see through the substrate 2 and thus to visualize the surface to be made up through the device 1 when this device is superposed on the said surface.

All of the coat 4 may, as illustrated, be superposed on the transparent area 5. In one variant, not shown, only part of the coat 4 is superposed on the transparent area 5.

The substrate 2 may be made of a transparent material. The transparent area 5 then extends over the entire surface of the substrate 2.

The substrate 2 may be made of a transparent material. The transparent area 5 then extends over the entire surface of the substrate 2.

In the illustrated example, the substrate 2 comprises a material as a transparent sheet bearing the transfer surface 3.

The substrate 2 may bear an indication 7, for example a print, which gives information regarding a recommended positioning for the makeup, for example "right cheek" as illustrated, or the nature of the keratin materials intended to be made up with the cosmetic ink of the coat 4, or the like, and may also provide information regarding the colour reference and/or the pattern.

The substrate 2 is preferably made of a flexible material. As a variant, the substrate 2 is made of a rigid or semi-rigid material.

All or part of the area of the transfer surface 3 superposed on the coat of cosmetic ink 4 is preferably smooth and has a roughness of less than or equal to 1 mm, especially between 1 and 100 μm and preferably less than or equal to 50 μm. The roughness is measured using a roughness meter, the tip of which has a radius of curvature of 10 mm, and the force of which, applied to the material to be characterized, is 6 mN.

FIGS. 3 to 5 schematically show various steps of an example of a makeup process according to the invention. As illustrated, the device 1 is first brought close to the area of skin P to be made up, which is preferably dry, so as to place the coat of ink 4 in contact with the area of skin P to be made up, and the user then applies a pressure allowing the cosmetic ink to be transferred onto the area of skin P to be made up. During the contact with the keratin materials, the substrate 2 is preferably not moved sideways so as not to affect the appearance of the transferred pattern.

The pattern transferred onto the keratin materials corresponds to the pattern formed by the coat 4 when it is present on the substrate 2 (i.e. when it has not yet been transferred onto the keratin materials to be made up).

In one example, not shown, the process also comprises a step of finishing makeup obtained on the keratin materials. The finishing is performed, for example, by rubbing the surface to be made up with the device 1 to obtain special effects.

FIG. 6 shows an embodiment example of a cosmetic assembly 10 according to the invention. This assembly comprises, in the same packaging, a plurality of devices 1 according to the invention which each differ by the pattern and/or colour formed by the coat 4. The packaging may be leaktight so as to prevent the inks from drying out. The packaging may be made with means for avoiding contact of the inks with a surface other than the transfer surface, so as to reduce the risk of premature transfer. For example, the packaging comprises a thermoformed shell whose wall extends a distance from the areas of the substrate that are covered with inks.

An example of a process for manufacturing a device according to the invention will now be described, with reference to FIG. 8.

In a first step 100, various patterns are proposed to the user, for example by displaying on a screen of a machine. Step 101 of choosing the pattern by the user may comprise an action such as pressing on a touchscreen in order to select the pattern intended to be printed.

The machine may also provide the user with a simulation of the makeup result. Thus, the machine may display a simulation of the appearance of the keratin materials made up with the chosen or produced pattern. To do this, the machine may acquire at least one image of the keratin materials to be made up.

In one variant, the user makes a computer file with the pattern that he wishes to print. In this case, the user may use drawing software for making such a pattern, and edit it, for example, in a file in .jpg image format.

Once the pattern has been chosen or made, the machine sends to the printer the data necessary for printing the pattern in step 102.

The machine may be connected physically and/or by means of a network to the printer performing the printing.

Once the data have been received, the pattern is printed in step 103.

The printer driver may comprise a menu for selecting a cosmetic ink cartridge among other cartridges installed in the printer and/or the nature of the substrate that is printed. As a variant, the printer automatically recognizes that the cartridge installed contains a cosmetic ink according to the invention and adjusts the operating parameters in consequence. The cartridge may thus comprise an identifier, for example an electronic chip, for providing the printer with information relating to the nature of the cosmetic ink that it contains, especially that this ink is of cosmetic nature.

In one embodiment example, the printer is configured to prohibit printing if the presence of a cartridge comprising a composition not intended to be placed in contact with human keratin materials, especially the skin, the nails or the lips, is detected.

As a variant, the printer may perform printing even if the presence of a cartridge comprising a composition not intended to be placed in contact with human keratin materials, especially the skin, in particular the scalp, the hair, the nails or the lips, is detected, this non-cosmetic ink cartridge possibly being used for printing on the substrate an indication relating to the cosmetic ink borne by the surface and/or the nature of the keratin materials to be made up.

The printing of the substrate may take place in several passes, to make successive deposits of ink at the same place, so as to increase the amount of ink deposited on the substrate. The substrate may effect, for example, between 1 and 20 passes in the printer and the amount of cosmetic ink dry matter deposited ranges, for example, from 0.01 mg/cm$^2$ to 100 mg/cm$^2$, or even from 0.1 mg/cm$^2$ to 10 mg/cm$^2$, better still from 0.2 mg/cm$^2$ to 10 mg/cm$^2$, in particular from 0.2 mg/cm$^2$ to 5 mg/cm$^2$.

The pattern may be monochromatic or, better still, polychromatic. In this case, printing may be performed at each passage in the printer with several cosmetic inks that are locally juxtaposed at the microscopic scale, depending on the colour to be reproduced. The printing resolution may be between 16 dpi and 1600 dpi.

The printer may be arranged to detect whether the ink previously deposited on the substrate is sufficiently dry before printing a new coat of ink, for example by measuring the electrical conduction between two points.

The printer and/or the printer driver may be made so as to inform the user of the need to wait a predefined time before performing a new printing on the already-printed substrate. The printer and/or the driver may automatically suspend the printing of an already-printed substrate if sufficient time has not passed to allow sufficient drying. The printer is preferably arranged so as not to deliver the printed substrate as long as all the coats of ink to be printed have not been printed.

FIG. 7 shows an embodiment example of a cosmetic assembly 20 according to the invention. The cosmetic assembly 20 comprises, in the same packaging:
a) a printer cartridge 21 containing a cosmetic ink according to the invention, and
b) a surface 3 intended to be printed with the cosmetic ink, for example defined by a substrate sheet.

This cosmetic assembly may be provided to the user, where appropriate, with the printer intended to use the cartridge.

In the illustrated example, the ink contained in the cartridge 21 comprises at least two dyes, of which at least one is hydrophilic and at least one other is hydrophobic.

Figure 9:
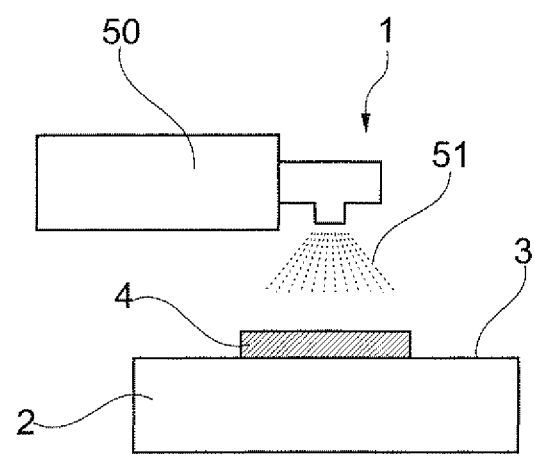

FIG. 9 shows another process variant according to the invention, in which a solvent such as water 51 is sprayed onto a coat of ink 4 printed on a surface 3 of a device example 1 according to the invention. The coat 4 was printed in the form of an emulsion or nanoemulsion, but is, for example, too dry to transfer correctly onto the keratin materials, in particular since it has lost its emulsion or nanoemulsion form. The solvent thus sprayed on moistens the coat and restores its emulsion or nanoemulsion form. Once the cosmetic ink of the coat 4 has regained its emulsion or nanoemulsion form, it is then placed in contact with the keratin materials. The solvent is sprayed, for example, using a pressurized container 50 of aerosol type, actuated by the user.

Figure 10:
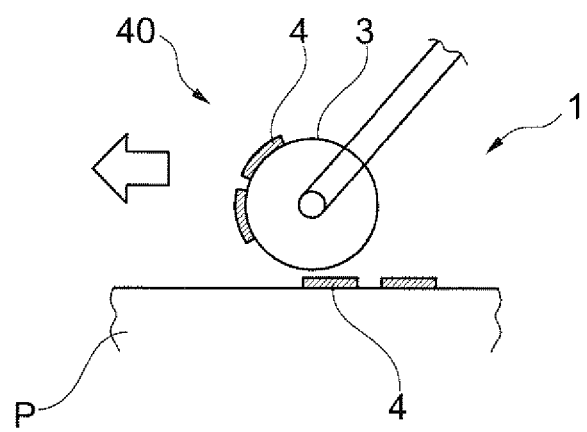
FIGS. 9 and 10 illustrate variants of the makeup process according to the invention.

FIG. 10 shows an embodiment variant of the device according to the invention in which the surface 3 consists of the outer surface of an applicator roller 40, for example the surface of a sheet of material borne by the applicator roller 40, on which the ink 4 is present. Such a surface may advantageously make it possible to perform transfer makeup application onto the hair or extended areas of the skin such as the back, the tummy or the legs.

EXAMPLES

Example 1: Nanoemulsion for an Inkjet Printer

Formula A

| | |
|---|---|
| Polyethylene glycol monoisostearate (8 EO) | 2% |
| Avocado oil | 5.25% |
| Jojoba oil | 5.25% |
| Cyclopentadimethylsiloxane | 3.5% |
| Polydimethyl/methylaminoethylaminopropylsiloxane in nanoemulsion form (SME 253 from Momentive Performance Materials) | 6% |
| Glycerol | 5% |
| Ethanol | 14% |
| Red 33 (CI 17200) | 1% |
| Water | qs 100% |

A nanoemulsion of formula A according to the invention is prepared via the high-pressure high-temperature mixer method.

It is used in a Canon Pixma IP100 inkjet printer to print a pattern on a transparent plastic printing sheet.

The sheet is left to dry for eight hours in the open air before being subsequently applied to the skin to transfer the pattern.

That transfer is performed without the presence of an intermediary compound.

Example 1a: Nanoemulsion for an Inkjet Printer

Formula B

| | |
|---|---|
| Polyethylene glycol monoisostearate (8 EO) | 2% |
| Behenyltrimethylammonium chloride | 2% |
| Avocado oil | 5.25% |
| Jojoba oil | 5.25% |
| Cyclopentadimethylsiloxane | 3.5% |
| Polydimethyl/methylaminoethylaminopropylsiloxane in nanoemulsion form (SME 253 from Momentive Performance Materials) | 6% |
| Glycerol | 5% |
| Ethanol | 14% |
| Curcumin | 3% |
| Water | qs 100% |

The same procedure as in Example 1 is used.

Example 2: Emulsion for an Inkjet Printer

Formula C

| (polyoxyethylene-2 polyoxypropylene-3 decyl ether (PPG 2 Deceth 3) | |
|---|---|
| (Emalex Dape 203 from Nihon Emulsion) | 5% |
| Isopropyl myristate | 5% |
| Red 33 (CI 17200) | 3% |
| Water | qs 100% |

An emulsion of formula C according to the invention is prepared by simple mixing.
It is used in a Canon Pixma IP100 inkjet printer to print a pattern on a transparent plastic printing sheet.
The sheet is left to dry for eight hours in the open air before being subsequently applied to the skin to transfer the pattern by simple contact.
The transfer is performed without the presence of an intermediary compound.

Example 2a: Emulsion for an Inkjet Printer

Formula D

| Oxyethylenated decyl alcohol (5 EO) | 18% |
|---|---|
| Isopropyl myristate | 6% |
| Curcumin | 3% |
| Water | qs 100% |

The expression "comprising a" should be understood as being synonymous with "comprising at least one".

The expression "between . . . and . . . " or "ranging from . . . to . . . " should be understood as including the limits.

The invention claimed is:

1. A process for manufacturing a device for applying a cosmetic product by transfer onto human keratin materials, comprising printing, using at least one digital printer, onto a transfer surface of the device a cosmetic ink, the cosmetic ink being in the form of an oil-in-water or water-in-oil emulsion comprising an emulsifier, the cosmetic ink being liquid at 20° C., wherein the cosmetic ink comprises an oily phase comprising at least one of
   esters of formula RCOOR' in which R represents a higher fatty acid residue comprising from 7 to 19 carbon atoms and R' represents a hydrocarbon-based chain comprising from 3 to 20 carbon atoms;
   $C_{14}$-$C_{22}$ fatty acids;
   decanol, fatty alcohols containing from 12 to 26 carbon atoms;
   liquid fatty acid triglycerides of 4 to 10 carbon atoms;
   isostearyl lactate, octyl hydroxystearate, octyldodecyl hydroxystearate, diisostearyl malate, triisocetyl citrate;
   propylene glycol dioctanoate, neopentyl glycol diheptanoate, diethylene glycol diisononanoate; and/or
   isododecane, isodecane, isohexadecane, decane, heptane, dodecane, cyclohexane,
the cosmetic ink being not entirety dry when borne by the transfer surface and before application to the keratin materials after a time of 15 minutes after printing, at 25° C. kept in contact with the air and a normal hygrometry of 55% relative humidity.

2. The process according to claim 1, the ink having a viscosity ranging from 1 mPa·s to 500 mPa·s, when measured at 25° C. according to a conventional process using a Rheomat 180 viscometer equipped with a spindle rotating at 200 rpm.

3. The process according to claim 1, the ink being in the form of a nanoemulsion comprising oil globules with a mean size of less than 100 nm.

4. The process according to claim 3, the ink being in the form of a nanoemulsion comprising an amphiphilic lipid, comprising at least one nonionic amphiphilic lipid.

5. The process according to claim 4, the nonionic amphiphilic lipid being chosen from:
   a) silicone surfactants,
   b) amphiphilic lipids that are liquid at a temperature of less than or equal to 45° C., chosen from esters of at least one polyol and of at least one fatty acid comprising at least one saturated or unsaturated, linear or branched $C_8$-$C_{22}$ alkyl chain,
   c) fatty acid esters of sugars and fatty alkyl ethers of sugars,
   d) surfactants that are solid at a temperature equal to 45° C., chosen from fatty esters of glycerol, fatty esters of sorbitan and oxyethylenated fatty esters of sorbitan, ethoxylated fatty ethers and ethoxylated fatty esters,
   e) block copolymers of ethylene oxide and of propylene oxide, and mixtures thereof.

6. The process according to claim 4, the nonionic amphiphilic lipids being present in the nanoemulsion in a mass content ranging from 0.2% to 12% by weight, relative to the total mass of the ink.

7. The process according to claim 4, the nanoemulsion comprising at least one ionic amphiphilic lipid, chosen especially from: alkali metal salts of dicetyl phosphate and of dimyristyl phosphate, alkali metal salts of cholesteryl sulfate, alkali metal salts of cholesteryl phosphate; lipoamino acids and salts thereof, the sodium salts of phosphatidic acid, phospholipids, alkylsulfonic derivatives, quaternary ammonium salts, fatty amines and salts thereof.

8. The process according to claim 4, the total mass content of nonionic and ionic amphiphilic lipids in the nanoemulsion ranging from 0.25% to 15% relative to the total mass of the nanoemulsion.

9. The process according to claim 1, the mass ratio of the oily phase relative to the total mass of the ink ranging from 2% to 40%.

10. The process according to claim 1, the oily phase comprising at least one oil with a molecular mass of greater than or equal to 400 g/mol.

11. The process according to claim 1, the coat of cosmetic ink being printed in a predefined pattern.

12. The process according to claim 1, the transfer surface on which the printing is performed being defined by all or part of: the outer surface of an applicator roller, the surface of an applicator pad, an element in sheet form, a patch, the surface of a porous foam, especially a sponge, a wipe, a coarse brush, a fine brush or a flocked tip.

13. The process according to claim 1, the transfer surface being an outer surface of a substrate, the substrate comprising information regarding the nature of the keratin materials intended to receive the cosmetic ink and/or the substrate comprising at least one translucent or transparent area.

14. The process according to claim 1, wherein the cosmetic ink comprises an oily phase comprising at least one of isododecane, isopropyl myristate, isostearyl alcohol, isodecyl neopentanoate, isononyl isononanoate, oleyl alcohol, 2-octyldodecanol, isopropyl palmitate, isopropyl isostearate, and mixtures thereof.

15. The process according to claim 1, the transfer surface being an outer surface of a substrate based on a non-absorbent material.

16. A process for manufacturing a device for applying a cosmetic product by transfer onto human keratin materials, comprising printing, using at least one digital printer, onto a transfer surface of the device a cosmetic ink, the cosmetic ink being in the form of an oil-in-water or water-in-oil emulsion comprising an emulsifier, the cosmetic ink being liquid at 20° C., wherein the cosmetic ink comprises an oily phase comprising at least one of esters of formula RCOOR' in which R represents a higher fatty acid residue comprising from 7 to 19 carbon atoms and R' represents a hydrocarbon-based chain comprising from 3 to 20 carbon atoms;

$C_{14}$-$C_{22}$ fatty acids;

decanol, fatty alcohols containing from 12 to 26 carbon atoms;

liquid fatty acid triglycerides of 4 to 10 carbon atoms;

isostearyl lactate, octyl hydroxystearate, octyldodecyl hydroxystearate, diisostearyl malate, triisocetyl citrate;

propylene glycol dioctanoate, neopentyl glycol diheptanoate, diethylene glycol diisononanoate; and/or isododecane, isodecane, isohexadecane, decane, heptane, dodecane, cyclohexane, the transfer surface being an outer surface of a substrate based on a non-absorbent material.

\* \* \* \* \*